US008697836B2

(12) United States Patent
Zanetti

(10) Patent No.: US 8,697,836 B2
(45) Date of Patent: Apr. 15, 2014

(54) COMPOSITION AND METHOD FOR INDUCING AND ENHANCING A TELOMERASE REVERSE TRANSCRIPTASE-REACTIVE CYTOTOXIC T LYMPHOCYTE RESPONSE

(75) Inventor: Maurizio Zanetti, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 83 days.

(21) Appl. No.: 12/150,164

(22) Filed: Apr. 25, 2008

(65) Prior Publication Data
US 2009/0074741 A1 Mar. 19, 2009

Related U.S. Application Data

(63) Continuation of application No. 09/788,110, filed on Feb. 15, 2001, now Pat. No. 7,388,071.

(60) Provisional application No. 60/182,685, filed on Feb. 15, 2000.

(51) Int. Cl.
*A61K 38/00* (2006.01)
*A61K 38/08* (2006.01)
*C07K 7/06* (2006.01)
*C07H 21/02* (2006.01)
*C07H 21/04* (2006.01)

(52) U.S. Cl.
USPC ......... 530/300; 530/328; 536/23.1; 536/23.2; 536/23.5

(58) Field of Classification Search
None
See application file for complete search history.

(56) References Cited

U.S. PATENT DOCUMENTS

| | | | |
|---|---|---|---|
| 4,622,952 | A | 11/1986 | Gordon |
| 5,508,386 | A | 4/1996 | Zanetti et al. |
| 5,583,202 | A | 12/1996 | Zanetti |
| 5,635,188 | A | 6/1997 | Bystryn |
| 5,658,234 | A | 8/1997 | Dunlavy |
| 5,658,762 | A | 8/1997 | Zanetti et al. |
| 5,962,320 | A | 10/1999 | Robinson |
| 6,093,809 | A | 7/2000 | Cech et al. |
| 6,106,829 | A | 8/2000 | He et al. |
| 6,168,946 | B1 | 1/2001 | Houghton et al. |
| 6,440,735 | B1 | 8/2002 | Gaeta |
| 6,992,176 | B2 | 1/2006 | Reiter et al. |
| 7,030,211 | B1 | 4/2006 | Gaudernack et al. |
| 7,078,416 | B2 | 7/2006 | Gaudernack et al. |
| 7,078,491 | B1 | 7/2006 | Harrington |
| 7,083,789 | B2 | 8/2006 | Ramakrishna et al. |
| 7,425,606 | B2 * | 9/2008 | Kosmatopoulos et al. ... 530/300 |

FOREIGN PATENT DOCUMENTS

| | | |
|---|---|---|
| EP | 1362597 B1 | 11/2003 |
| WO | WO 94/03205 | 2/1994 |
| WO | WO 99/50392 | 10/1999 |
| WO | WO-99/63945 A2 | 12/1999 |
| WO | WO 00/02581 | 1/2000 |
| WO | WO 00/25813 | 5/2000 |
| WO | WO 00/61766 | 10/2000 |

OTHER PUBLICATIONS

Mattes et al. (1983) "A Pigmentation-associated, Differentiation Antigen of Human Melanoma Defined by a Precipitating Antibody in Human Serum," Int. J. Cancer 32:717.
Tai et al. (1983) "Glycoproteins as Differentiation Markers in Human Malignant Melanoma and Melanocytes," Cancer Res. 43:2773.
Thomson et al. (1988) "Differentiation Antigens of Melanocytes and Melanoma: Analysis of Melanosome and Cell Surface Markers of Human Pigmented Cells with Monoclonal Antibodies," J. Invest. Dermatol. 90:459.
Zakian (1995) "Telomeres: Beginning to Understand the End," Science 270:1601.
Blackburn and Gall (1978) "A Tandemly Repeated Sequence at the Termini of the Extrachromosomal Ribosomal RNA Genes in *Tetrahymena*," J. Mol. Biol. 120:33.
Oka el al. (1980) "Inverted terminal repeat sequence in the macronuclear DNA of *Stylonychia pustulata*," Gene 10:301.
Klobutcher et al. (1981) "All gene-sized DNA molecules in four species of hypotrichs have the same terminal sequence and an unusual 3' terminus," Proc. Natl. Acad. Sci. 78:3015.
Wellinger et al. (1993) "Origin Activation and Formation of Single-Strand $TG_{1-3}$ Tails Occur Sequentially in Late S Phase on a Yeast Linear Plasmid," Mol. Cell. Biol. 13:4057.
Minev et al. (2000) "Cytotoxic T cell immunity against telomerase reverse transcriptase in humans," Proc. Natl. Acad. Sci. USA 97:4796-4801.
Vonderheide et al. (1999) "The Telomerase Catalytic Subunit Is a Widely Expressed Tumor-Associated Antigen Recognized by Cytotoxic T Lymphocytes," Immunity 10:673-679.
Blackburn (1992) "Telomerases," Ann. Rev. Biochem. 61:1139-129.
Blackburn (1991) "Structure and function of telomeres," Nature 350:569-73.
Greider (1994) "Mammalian teleomere dynamics: healing, fragmentation shortening and stabilization," Curr. Opin. Genet. Devel. 4:203-11.
Counter et al. (1992) "Telomere shortening associated with chromosome instability is arrested in immortal cells which express telomerase activity," EMBO J. 11:1921-29.
Buchkovich et al. (1996) "Telomerase Regulation during Entry into the Cell Cycle in Normal Human T Cells," Mol. Biol. Cell 7:1443-54.
Weng et al. (1996) "Regulated Expression of Telomerase Activity in Human T Lymphocyte Development and Activation," J. Exp. Med. 183:2471-9.
Weng et al. (1997) "Telomere lengthening and telomerase activation during human B cell differentiation," Proc. Natl. Acad. Sci. USA 94:10827-32.
Lee et al. (1998) "Essential role of mouse telomerase in highly proliferative organs," Nature 392:569-74.
Kim et al. (1994) "Specific Association of Human Telomerase Activity with Immortal Cells and Cancer," Science 266:2011-5.

(Continued)

*Primary Examiner* — Peter J Reddig
(74) *Attorney, Agent, or Firm* — Morrison & Foerster LLP

(57) ABSTRACT

Telomerase peptides that bind MHC are disclosed. The instant application also discloses vaccines containing said peptides and methods of using said peptides to enhance a CTL response against mammalian cancer cells.

12 Claims, 10 Drawing Sheets

(56) References Cited

OTHER PUBLICATIONS

Meyerson et al. (1997) "hEST2, the Putative Human Telomerase Catalytic Subunit Gene, is Up-Regulated in Tumor Cells and during Immortalization," Cell 90:785-795.

Bodnar et al. (1998) "Extension of Life-Span by Introduction of Telomerase into Normal Human Cells," Science 279:349-52.

Rudolph et al (1999) "Longevity, Stress Response, and Cancer in Aging Telomerase-Deficient Mice," Cell 96:701-12.

Greenberg et al. (199) "Short Dysfunctional Telomeres Impair Tumorigenesis in the INK4a$^{\Delta 2/3}$ Cancer-Prone Mouse," Cell 97:515-25.

Morales et al. (1999) "Absence of cancer-associated changes in human fibroblasts immortalized with telomerase," Nature Genetics 21:115-8.

Hahn et al. (1999) "Creation of human tumour cells with defined genetic elements," Nature 400:464-8.

Broccoli et al. (1995) "Telomerase activity in normal and malignant hematopoietic cells," Proc. Natl. Acad. Sci. USa 92:9082-6.

Shay et al. (1997) "A Survey of Telomerase Activity in Human Cancer," Eur. J. Cancer 33:787-91.

Kim (1997) "Clinical Implications of Telomerase in Cancer," Eur. J. Cancer 33:-781-6.

Nakamura et al. (1997) "Telomerase Catalytic Subunit Homologs from Fission Yeast and Human," Science 277:955-9.

Marx (1993) "How p53 Suppresses Cell Growth." Science 262:1644-5.

Disis et al. (1997) "HER-2/neu Protein: A Target for Antigen-Specific Immunotherapy of Human Cancer," Adv. Cancer Res. 71:343-71.

Walker et al. (1988) "HIV-1 Reverse Transcriptase Is a Target for Cytotoxic T Lymphocytes in Infected Individuals," Science 240:64-6.

Schwartz (1990) "A Cell Culture Model for T Lymphocyte Clonal Anergy," Science 248:1349-56.

Firat et al. (1999) "H-2 class I knockout, HLA-12.1-transgenic mice: a versatile animal model for preclinical evaluation of antitumor immunotherapeutic strategies," Eur. J. Immunol. 29:3112-21.

Lee (1990) in *The HLA System*, ed. Lee, J. (Springer-Verlag, NY), pp. 141-178.

Fernandez-Vina et al. (1992) "DNA Typing for HLA Class I Alleles, 1. Subsets of HLA-A2 and of -A28," Human Immunol. 33:163-73.

Krausa et al. (1995) "Genetic polymorphism within HLA-A*02: significant allelic variation revealed in different populations," Tissue Antigens 45:223-31.

Ruppert et al. (1993) "Prominent Role of Secondary Anchor Residues in Peptide Binding to HLA-A2.1 Molecules," Cell. 74:929-37.

Parker et al. (1994) "Scheme for Ranking Potential HLA-A2 Binding Peptides Based on Independent Binding of Individual Peptide Side-Chains," J. Immunol. 152:163-75.

Vitiello et al. (1991) "Analysis of the HLA-restricted Influenza-specific Cytotoxic T Lymphocyte Response in Transgenic Mice Carrying a Chimeric Human-Mouse Class I Major Histocompatibility Complex," J. Exp. Med. 173:1007-15.

Sette et al. (1994) "The Relationship Between Class I Binding Affinity and Immunogenicity of Potential Cytotoxic T Cell Epitopes," J. Immunol. 153:5586-92.

van der Burg et al. (1996) "Immunogenicity of Peptides Bound to MHC Class I Molecules Depends on the MHC-Peptide Complex Stability," J. Immunol. 156:3308-14.

Sommerfeld el al. (1996) "Telomerase Activity: A Prevalent Marker of Malignant Human Prostate Tissue," Cancer Res. 56:218-22.

Hunt et al. (1992) "Characterization of Peptides Bound to the Class I MHC Molecule HLA-A2.1 by Mass Spectrometry," Science 1261-3.

Quaranta et al. (1982) "A Recurrent Idiotype on Monoclonal Anti-Human Ia Antibodies," J. Exp. Med. 156:1551-6.

Zanetti et al. (1993) "Expression of conformationally constrained adhesion peptide in an antibody CDR loop and inhibition of natural killer cell cytotoxic activity by an antibody antigenized with the RGD motif," EMBO J. 12:4375-4384.

Hiyama et al. (1995) "Activation of Telomerase in Human Lymphocytes and Hematopoietic Progenitor Cells," J. Immunol. 155:3711-15.

Pascolo et al. (1997) "HLA-A2.1-restricted Education and Cytolytic Activity of CD8$^+$T Lymphocytes from β2 Microglobulin (β2m) HLA-A2.1 Monochain Transgenic H-2D$^b$ β2m Double Knockout Mice," J. Exp. Med. 185:2043-51.

Doyle et al. (1985) "Markedly Decreased Expression of Class I Histocompatibility Antigens, Protein, and mRNA in Human Small-Cell Lung Cancer," J. Exp. Med. 161:1135-51.

Momburg et al. (1986) "Loss of HLA-A,B,C and *De Novo* Expression of HLA-D in Colorectal Cancer," Int. J. Cancer 37:179-84.

Restifo et al. (1993) "Identification of Human Cancers Deficient in Antigen Processing," J. Exp. Med. 177:265-72.

Cromme et al. (1994) "Loss of Transporter Protein, Encoded by the TAP-1 Gene, is Highly Correlated with Loss of HLA Expression in Cervical Carcinomas," J. Exp. Med. 179:335-40.

Rosenberg et al. (1998) "Immunologic and therapeutic evaluation of a synthetic peptide vaccine for the treatment of patients with metastatic melanoma," Nature Med. 4:321-27.

Nestle et al. (1998) "Vaccination of melanoma patients with peptide- or tumor lysate-pulsed dendritic cells," Nature Med. 4:328-332.

Thomson et al. (1998) "Delivery of Multiple CD8 Cytotoxic T Cell Epitopes by DNA Vaccination," J. Immunol. 160:1717-23.

Sykulev et al. (1996) "Evidence that a Single Peptide-MHC Complex on a Target Cell Can Elicit a Cytolytic T Cell Response," Immunity 4:565-71.

Morgan et al. (1998) "Activation of Low Avidity CTL Specific for a Self Epitope Results in Tumor Rejection But Not Autoimmunity," J. Immunol. 160:643-51.

Overwijk et al. (1999) "Vaccination with a recombinant vaccinia virus encoding a "self" antigen induces autoimmune vitiligo and tumor cell destruction in mice: Requirement for CD4$^+$T lymphocytes," Proc. Natl. Acad. Sci. USA 96:2982-7.

Hu et al. (1993) "An Evulation of the Potential to Use Tumor-associated Antigens as Targets for Antitumor T Cell Therapy Using Transgenic Mice Expressing a Retroviral Tumor Antigen in Normal Lymphoid Tissues," J. Exp. Med. 177:1681-90.

Uyttenhove el al. (1997) "The Expression of Mosue Gene *P1A* in Testis Does Not Prevent Safe Induction of Cytolytic T Cells Against a P1A-Encoded Tumor Antigen," Int. J. Cancer 70:349-56.

Falk et al. (1991) "Allele-specific motifs revealed by sequencing of self-peptides eluted from MHC molecules," Nature 351:290-6.

Rotzschke et al. (1990) "Isolation and analysis of naturally processed viral peptides as recognized by cytotoxic T cells," Nature 348:252-254.

Schumacher et al. (1991) "Peptide selection by MHC class I molecules," Nature 350:703-6.

Vonderheide et al., "Search for universal tumor antigens: Potential of the catalytic telomerase subunit," *Blood*, 92(10Supp):500A, abstract# 2058 (Nov. 15, 1998).

Vonderheide et al., "Generation of telomerase-specific HLA-A3-restricted cytotoxic T lymphocytes from patient blood: Implications for widely applicable anti-cancer immunotherapy," *Blood*, 94(10Supp):677A, abstract #2999 (Nov. 15, 1999).

Adotevi et al. (2006) "Immunogenic HLA-B*0702-restricted epitopes derived from human telomerase reverse transcriptase that elicit antitumor cytotoxic T-cell responses," Clin Can Res 12:3158-3167.

Amarnath et al. (2004). "In vitro quantification of the sytotoxic T lymphocyte response against human telomerase reverse transcripase in breast cancer," *Int J Oncol* 25:211. [abstract only].

Arai et al (2001). "Identification of human telomerase reverse transcriptase-derived peptides that induce HLA-A24-restricted anti-leukemia cytotoxic T lymphocytes," *Blood* 97:2903-2907.

Ayyoub et al. (2001). "Lack of tumor recognition by hTERT peptide 540-548-specific CD8(+) T cells from melanoma patients reveals inefficient antigen processing." *Eur J Immunol*, 31:2642-2651.

Cortez-Gonzalez et al. (2006). "Immunogenic HLA-B7-restricted peptides of hTRT," *International Immunology* 18:1707-1718.

Cortez-Gonzalez et al. (2007). "Telomerase immunity from bench to bedside: round one," *J Transl Med* 26:12-29.

(56) References Cited

OTHER PUBLICATIONS

Doytchinova et al. (2004). "Identifying human MHC supertypes using bioinformatic methods," *J Immunol* 172:4314-4323.
European Search Report mailed Feb. 5, 2010, for EP Application No. 07749019.1 filed Aug. 19, 2008, 10 pages.
Falk et al. (1991) "Allele-specific Motifs Revealed by Sequencing of Self-peptides Eluted from MHC Molecules," *Nature* 351:290-296.
Filiaci et al. (2006) "Frequency of telomerase-specific CD8+ T lymphocytes in patients with cancer," *Blood* 107:1505-1512.
Gross et al. (2004). "High vaccination efficiency of low-affinity epitopes in antitumor immunotherapy," *J Clin Invest* 113:425-433.
Hernandez et al. (2002). "Identification of a human telomerase reverse transcriptase peptide of low affinity for HLA-A2.1 that induces cytotoxic T lymphocytes and mediates lysis of tumor cells." *PNAS USA* 99:12275-12280.
Hernandez et al. (2004). "Antigenicity and immunogenicity of peptide analogues of a low affinity peptide of the human telomerase reverse transcriptase tumor antigen," *Eur J Immunol*, 34:2331-2341.
International Preliminary Report on Patentability mailed Aug. 14, 2008, for PCT Application No. PCT/US2007/01587 filed Jan. 19, 2007, 6 pages.
International Search Report mailed Aug. 14, 2008, for PCT Application No. PCT/US2007/01587 filed Jan. 19, 2007, 3 pages.
Kuttler et al. (2000). "An algorithm for the prediction of proteasomal cleavages," *J Mol Biol* 298:417-29. [abstract only].
Lee et al. (1999). "Increased Vaccine-specific T cell Frequency after Peptide-based Vaccination Correlates with Increased Susceptibility to in vitro Stimulation but does not Lead to Tumor Regression," *J Immunol* 163:6292-6300.
Nair (2000). "Induction of cytotoxic T cell responses and tumor immunity against unrelated tumors using telomerase reverse transcriptase RNA transfected dendritic cells," *Nature Medicine* 6(8):1011-1017.
Nussbaum et al. (2001). "PAProC: a prediction algorithm for proteasomal cleavages available on the WWW," *Immunogenetics* 53:87-94. [abstract only].
Overwijk et al. (1998). "gp100/pmel 17 is a murine tumor rejection antigen: induction of "self"-reactive, tumoricidal T cells using high-affinity, altered peptide ligand," *J Exp Med* 188:277-86.
Rammensee et al. (1999). "SYFPEITHI: database for MHC ligands and peptide motifs," *Immunogenetics* 50:213-9.
Rankpep: Prediction of MHC-restricted Ligands, located at <http://mif.dfci.harvard.edu/Tools/rankpep.sub.--help.html>, last visited on Feb. 3, 2006, pp. 1-12.
Rohrlich et al. (2003). "HLA-B*0702 transgenic, H-2KbDb double-knockout mice: phenotypical and functional characterization in response to influenza virus," *Int Immunol* 15:765-72.
Scardino et al. (2002) "HER-2/neu and hTERT cryptic epitopes as novel targets for broad spectrum tumor immunotherapy," *J Immunol* 168:5900-5906.
Sette and Sidney (1999). "Nine major HLA class I supertypes account for the vast preponderance of HLA-A and -B polymorphism," *Immunogenetics* 50:201-12.
Sidney et al. (1995). "Several HLA alleles share overlapping peptide specificities," *J Immunol* 154:247-59.
Sidney et al. (1996). "Specificity and degeneracy in peptide binding to HLA-B7-like class I molecules," *J Immunol* 157:3480-3490.
Slansky et al. (2000). "Enhanced antigen-specific antitumor immunity with altered peptide ligands that stabilize the MHC-peptide-TCR complex," *Immunity* 13:529-38.
Su et al. (2003). "Immunological and clinical responses in metastatic renal cancer patients vaccinated with tumor RNA-transfected dendritic cells," *Cancer Res* 63:2127-33.
Su at al. (2005). "Telomerase mRNA-transfected dendritic cells stimulate antigen-specific CD8+ and CD4+ T cell responses in patients with metastatic prostate cancer," *J Immunol* 174:3798-807.
Tangri et al. (2001). "Structural features of peptide analogs of human histocompatibility leukocyte antigen class I epitopes that are more potent and immunogenic than wild-type peptide," *J Exp Med* 194:833-46.
Vonderheide et al. (2001). "Characterization of HLA-A3-restricted cytotoxic T lymphocytes reactive against the widely expressed tumor antigen telomerase," *Clin Cancer Res* 7:3343-3348.
Vonderheide et al. (2001). "Equivalent induction of telomerase-specific cytotoxic T lymphocytes from tumor-bearing patients and healthy individuals." *Cancer Res* 61:8366-8370.
Vonderheide et al. (2002). "Telomerase as a universal tumor-associated antigen for cancer immunotherapy," *Oncogene* 21:674-679.
Vonderheide et al. (2004). "Vaccination of cancer patients against telomerase induces functional antitumor CD8+ T lymphocytes," *Clin Cancer Res* 10:828-39.

* cited by examiner

```
   1  MPRAPRCRAV  RSLLRSHYRE  VLPLATFVRR  LGPQGWRLVQ  RGDPAAFRAL  VAQCLVCVPW
  61  DARPPPAAPS  FRQVSCIKEL  VARVLQRLCE  RGAKNVLAFG  FALLDGARGG  PPEAFTTSVR
 121  SYLPNTVTDA  LRGSGAWGIL  LRRVGDDVLV  HLLARCALFV  LVAPSCAYQV  CGPPLYQLGA
 181  ATQARPPPHA  SGPRRRLGCE  RAWNHSVREA  GVPLGLPAPG  ARRRGGSASR  SLPLPKRPRR
 241  GAAPEPERTP  VGQGSWAHPG  RTRGPSDRGF  CVVSPARPAE  EATSLEGALS  GTRHSHPSVG
 301  RQHHAGPPST  SRPPRPWDTP  CPPVYAETKH  FLYSSGDKEQ  LRPSFLSSL  RESITGARRL
 361  VTIFLGSRP  WMPGTPRRLP  RLPQRYWQMR  PLFLELLGNH  AQCPYGVLLK  THCPLRAAVT
 421  PAAGVCAREK  PQGSVAAPEE  EDTDPRRLVQ  LLRQHSSPWQ  VYGFVRACLR  RLVPPGLWGS
 481  RHNERRFLRN  TKKFISLGKH  AKLSLQELTW  KMSVRDCAWL  RRSPGVGCVP  AAEHRLREEI
 541  LAKFLHWEMS  VYVVELRSF  FYVTETTFQK  NRLFFYRKSV  WSKLQSIGIR  QHLKRVQLRE
 601  LSEAEVRQHR  EARPALLTSR  LRFIPKPDGL  RPIVNMDYVV  RTFVLRVRAQ  GARTFRREKR  AERLTSRVKA
 661  LFSVLNYERA  RRPGLLGASV  LGLDDIHRAW  AHGHVRKAFK  DPPPELYFVK  VDVIGAYDTI
 721  PQDRLTEVIA  SIIKPQNTYC  VRRYAVVQKA  ASSGLEDVEL  SHVSTLTDLQ  PYMRQFVAHL
 781  QETSPLRDAV  VIEQSSINE  NKLFAGIRRD  GLLIRLVDDF  RGKSYVQCQG  IPQGSIISTL
 841  LCSICYGDME  NKLFAGIRRD  GLLIRLVDDF  LVTPHLTHA  KTFLRTLVRG  VPEYGCVVNL
 901  RKTVVNFPVE  DEALGGTAFV  QMPAHGLFPW  CGLLLDTRTL  EVQSDYSSYA  RTSIRASLTF
 961  NRGFKAGRNM  RRKLFGVLRL  KCHSLFLDLQ  VNSLQIVCTN  IYKILLQAY  RFHACVLQLP
1021  FHQQVWKNPT  FFLRVISDTA  SLCYSILKAK  NAGMSLGAKG  AAGPLPSEAV  QWLCHQAELL
1081  KLTRHRVTYV  PLLGSLRTAQ  TQLSRKLPGT  TLTALEAAAN  PALPSDFKTI  LD  1132
```

"L" at position 2, L or I at position 9

"L" at position 2, "V" at position 9

"M" at position 2, "V, L or I" at position 9

Figure 5

SEQUENCE LISTING

<160> NUMBER OF SEQ ID NOS: 23

<210> SEQ ID NO 1
<211> LENGTH: 9
<212> TYPE: PRT
<213> ORGANISM: Homo sapiens

<400> SEQUENCE: 1

Ile Leu Ala Lys Phe Leu His Trp Leu
1               5

```
<210> SEQ ID NO 2
<211> LENGTH: 9
<212> TYPE: PRT
<213> ORGANISM: Homo sapiens

<400> SEQUENCE: 2

Arg Leu Val Asp Asp Phe Leu Leu Val
1               5

<210> SEQ ID NO 3
<211> LENGTH: 9
<212> TYPE: PRT
<213> ORGANISM: Homo sapiens

<400> SEQUENCE: 3

Ala Ala Gly Ile Gly Ile Leu Thr Val
1               5

<210> SEQ ID NO 4
<211> LENGTH: 13
<212> TYPE: PRT
<213> ORGANISM: Hepatitis B virus

<400> SEQUENCE: 4

Thr Pro Pro Ala Tyr Arg Pro Pro Asn Ala Pro Ile Leu
1               5                   10

<210> SEQ ID NO 5
<211> LENGTH: 9
<212> TYPE: PRT
<213> ORGANISM: Homo sapiens

<400> SEQUENCE: 5

Tyr Leu Ser Gly Ala Asn Leu Asn Leu
1               5

<210> SEQ ID NO 6
<211> LENGTH: 10
<212> TYPE: PRT
<213> ORGANISM: Homo sapiens

<400> SEQUENCE: 6

Val Leu Tyr Arg Tyr Gly Ser Phe Ser Val
1               5                   10

<210> SEQ ID NO 7
<211> LENGTH: 9
<212> TYPE: PRT
<213> ORGANISM: HIV-1

<400> SEQUENCE: 7

Ile Leu Lys Glu Pro Val His Gly Val
1               5

<210> SEQ ID NO 8
<211> LENGTH: 9
<212> TYPE: PRT
<213> ORGANISM: Homo sapiens

<400> SEQUENCE: 8

Leu Leu Ala Arg Cys Ala Leu Phe Val
1               5

<210> SEQ ID NO 9
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 9

Val Leu Ala Phe Gly Phe Ala Leu Leu
1               5

<210> SEQ ID NO 10
<211> LENGTH: 9
<212> TYPE: PRT
<213> ORGANISM: Homo sapiens

<400> SEQUENCE: 10

Leu Leu Gly Ala Ser Val Leu Gly Leu
1               5

<210> SEQ ID NO 11
<211> LENGTH: 9
<212> TYPE: PRT
<213> ORGANISM: Homo sapiens

<400> SEQUENCE: 11

Arg Leu Thr Glu Val Ile Ala Ser Ile
1               5

<210> SEQ ID NO 12
<211> LENGTH: 9
<212> TYPE: PRT
<213> ORGANISM: Homo sapiens

<400> SEQUENCE: 12

Ser Leu Asn Glu Ala Ser Ser Gly Leu
1               5

<210> SEQ ID NO 13
<211> LENGTH: 9
<212> TYPE: PRT
<213> ORGANISM: Homo sapiens

<400> SEQUENCE: 13

Ile Leu Ser Thr Leu Leu Cys Ser Leu
1               5

<210> SEQ ID NO 14
<211> LENGTH: 9
<212> TYPE: PRT
<213> ORGANISM: Homo sapiens

<400> SEQUENCE: 14

Gly Leu Phe Pro Trp Cys Gly Leu Leu
1               5

<210> SEQ ID NO 15
<211> LENGTH: 9
<212> TYPE: PRT
<213> ORGANISM: Homo sapiens

<400> SEQUENCE: 15

Trp Leu Cys His Gln Ala Phe Leu Leu
1               5

<210> SEQ ID NO 16
<211> LENGTH: 9
```

```
<212> TYPE: PRT
<213> ORGANISM: Homo sapiens

<400> SEQUENCE: 16

Arg Leu Phe Phe Tyr Arg Lys Ser Tyr
1               5

<210> SEQ ID NO 17
<211> LENGTH: 9
<212> TYPE: PRT
<213> ORGANISM: Homo sapiens

<400> SEQUENCE: 17

Phe Met Cys His His Ala Val Arg Ile
1               5

<210> SEQ ID NO 18
<211> LENGTH: 9
<212> TYPE: PRT
<213> ORGANISM: Homo sapiens

<400> SEQUENCE: 18

Tyr Leu Ala Arg Cys Ala Leu Phe Val
1               5

<210> SEQ ID NO 19
<211> LENGTH: 9
<212> TYPE: PRT
<213> ORGANISM: Homo sapiens

<400> SEQUENCE: 19

Glu Leu Leu Arg Ser Phe Phe Tyr Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Tyr Leu Leu Arg Ser Phe Phe Tyr Val
1               5

<210> SEQ ID NO 21
<211> LENGTH: 9
<212> TYPE: PRT
<213> ORGANISM: Homo sapiens

<400> SEQUENCE: 21

Arg Leu Phe Phe Tyr Arg Lys Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Tyr Leu Phe Phe Tyr Arg Lys Ser Val
1               5

<210> SEQ ID NO 23
```

<211> LENGTH: 1132
<212> TYPE: PRT
<213> ORGANISM: Homo sapiens

<400> SEQUENCE: 23

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400
```

```
Ala Gln Cys Pro Tyr Gly Val Leu Leu Lys Thr His Cys Pro Leu Arg
            405                 410                 415
Ala Ala Val Thr Pro Ala Ala Gly Val Cys Ala Arg Glu Lys Pro Gln
        420                 425                 430
Gly Ser Val Ala Ala Pro Glu Glu Asp Thr Asp Pro Arg Arg Leu
            435                 440                 445
Val Gln Leu Leu Arg Gln His Ser Ser Pro Trp Gln Val Tyr Gly Phe
450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Glu Ile Leu Ala Lys Phe
530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
```

-continued

```
                    820             825             830
Gln Gly Ser Ile Leu Ser Thr Leu Leu Cys Ser Leu Cys Tyr Gly Asp
            835             840             845
Met Glu Asn Lys Leu Phe Ala Gly Ile Arg Arg Asp Gly Leu Leu Leu
        850             855             860
Arg Leu Val Asp Asp Phe Leu Leu Val Thr Pro His Leu Thr His Ala
865             870             875             880
Lys Thr Phe Leu Arg Thr Leu Val Arg Gly Val Pro Glu Tyr Gly Cys
                885             890             895
Val Val Asn Leu Arg Lys Thr Val Val Asn Phe Pro Val Glu Asp Glu
                900             905             910
Ala Leu Gly Gly Thr Ala Phe Val Gln Met Pro Ala His Gly Leu Phe
            915             920             925
Pro Trp Cys Gly Leu Leu Leu Asp Thr Arg Thr Leu Glu Val Gln Ser
        930             935             940
Asp Tyr Ser Ser Tyr Ala Arg Thr Ser Ile Arg Ala Ser Leu Thr Phe
945             950             955             960
Asn Arg Gly Phe Lys Ala Gly Arg Asn Met Arg Arg Lys Leu Phe Gly
                965             970             975
Val Leu Arg Leu Lys Cys His Ser Leu Phe Leu Asp Leu Gln Val Asn
                980             985             990
Ser Leu Gln Thr Val Cys Thr Asn Ile Tyr Lys Ile Leu Leu Leu Gln
            995             1000            1005
Ala Tyr Arg Phe His Ala Cys Val Leu Gln Leu Pro Phe His Gln
        1010            1015            1020
Gln Val Trp Lys Asn Pro Thr Phe Phe Leu Arg Val Ile Ser Asp
        1025            1030            1035
Thr Ala Ser Leu Cys Tyr Ser Ile Leu Lys Ala Lys Asn Ala Gly
        1040            1045            1050
Met Ser Leu Gly Ala Lys Gly Ala Ala Gly Pro Leu Pro Ser Glu
        1055            1060            1065
Ala Val Gln Trp Leu Cys His Gln Ala Phe Leu Leu Lys Leu Thr
        1070            1075            1080
Arg His Arg Val Thr Tyr Val Pro Leu Leu Gly Ser Leu Arg Thr
        1085            1090            1095
Ala Gln Thr Gln Leu Ser Arg Lys Leu Pro Gly Thr Thr Leu Thr
        1100            1105            1110
Ala Leu Glu Ala Ala Ala Asn Pro Ala Leu Pro Ser Asp Phe Lys
        1115            1120            1125
Thr Ile Leu Asp
        1130
```

COMPOSITION AND METHOD FOR INDUCING AND ENHANCING A TELOMERASE REVERSE TRANSCRIPTASE-REACTIVE CYTOTOXIC T LYMPHOCYTE RESPONSE

This application is a continuation of U.S. application Ser. No. 09/788,110, filed Feb. 15, 2001, now U.S. Pat. No. 7,388,071, which claims priority to U.S. Provisional Application No. 60/182,685, filed Feb. 15, 2000.

BACKGROUND OF THE INVENTION

1. Field of the Invention

The present invention concerns vaccines effective for treating cancer. This invention particularly concerns a universal cancer vaccine involving telomerase reverse transcriptase as a specific tumor antigen, a method for its use for targeting cytotoxic T lymphocytes to tumor cells, and a method for induction and/or augmentation of a cancer patient's immune response against his tumor.

2. Description of the Prior Art

Various publications are referenced within this application. The disclosures within these publications are hereby incorporated by reference, in their entireties, into this application so that the state of art to which this invention pertains is more fully described.

The prevalent cancer treatments of choice heretofore are surgery, radiation, chemotherapy or a combination thereof. With the exception of a very few cancers, prognosis has not been very satisfactory, resulting in death of the patient after sometimes horrendous suffering from the treatments themselves.

Many medical research laboratories throughout the world are doing research directed towards developing effective, non-invasive treatments for arresting the growth and destroying both benign and malignant tumors. However, treatments employed, both in clinical trials or general practice, have not demonstrated appreciable levels of tumor cell necrosis thus far.

Aspecific Methods of Treatment

One method for treating tumors, brachytherapy, involves injecting microscopic clumps of the protein albumin directly into the tumor. A suitable amount of radioactive phosphorous is then added through the same needle. The albumin clogs capillaries within the tumor, thereby, preventing the release of radioactive phosphorous to tissues outside the tumor. Tumor cells take up and use the phosphorous rapidly, selectively killing them with radioactivity without damaging normal cells in other parts of the body. By the time the capillaries become unclogged, all or most of the radioactive phosphorous has been absorbed by the cells comprising the tumor, leaving little to escape into adjacent tissue. This therapy, however, is difficult to implement and always carries the danger of radioactive material escaping into healthy parts of the body causing serious damage.

Robert T. Gordon in U.S. Pat. No. 4,622,952 disclosed a different method for treating tumors. This method attempts to take advantage of the observed different heat sensitivity between tumor and normal cells. It is well known that tumor cells are killed at lower temperatures than normal cells. Thus, Gordon proposed a method using electromagnetic energy to elevate the temperature of tumor cells or tissues, to kill the tumor cells without seriously affecting normal cells.

Immunotherapy

1. Antibody Response

Many attempts have been made to kill tumor cells with polyclonal or monoclonal isoantibodies or autologous antibodies elicited against tumor-specific antigens. Generally, this method is not successful, especially when dealing with solid tumors.

2. Cytotoxic Immunity

Unfortunately, these approaches for the prevention and/or treatment of cancer have not been successful or completely satisfactory because of a number of problems, such as the absence in the vaccine of tumor antigens expressed by the tumor to be treated, poor characterization of the antigens in tumor vaccines, the contamination of vaccines by immunogenic but undesirable material, such as fetal calf serum (FCS) protein or transplantation antigens and additionally due to the antigenic heterogenicity of the cancer cells. Moreover, such tumor vaccines were often prepared from fresh tumor cells, the supply of which is limited so that the properties of the vaccines are not reproducible.

3. Current Concepts

Selecting an Aspecific Target Substance.

U.S. Pat. No. 5,658,234, issued to Dunlavy in 1997 describes a method for treating a tumor comprising the steps of selecting a target substance which has at least one component with an atomic or molecular resonance frequency or frequencies different from the atomic, molecular or cellular resonant frequencies of normal cells, locating or depositing the target substance within the tumor, and irradiating the target substance with electromagnetic wave energy at a frequency or frequencies corresponding to the atomic or molecular resonance of the component such that the component absorbs energy from the electromagnetic wave, resulting in the release of heat sufficient to destroy, terminate or slow the growth of the tumor without adversely affecting the viability of normal cells.

a. Specific Melanoma Antigens

Melanosomal antigens can be recognized by the immune system. This has been demonstrated by immunoprecipitation of a gp75 antigen from autologous melanoma cells by serum IgG antibodies of a patient with metastatic melanoma (Mattes, J. M., T. M. Thomson, L. J. Old, and K. O. Lloyd. (1983) A pigmentation associated, differentiation antigen of human melanoma defined by a precipitating antibody in human serum, Int. J. Cancer. 32:717). The gp75 antigen is a melanosomal polypeptide that is the most abundant glycoprotein synthesized by pigmented melanocytes and melanomas. (Tai, T., M. Eisinger, S. Ogata, and K. O. Lloyd. (1983) Glycoproteins as differentiation markers in human malignant melanoma and melanocytes, Cancer Res. 43:2773). Epidermal melanocytes, benign pigmented lesions, and primary and metastatic melanomas express gp75, but other cell types do not (Thomson, T. M., F. X. Real, S. Murakami, C. Cardon-Cardo, L. J. Old, and A. N. Houghton. (1988) Differentiation antigens of melanocytes and melanoma: Analysis of melanosome and cell surface markers of human pigmented cells with monoclonal antibodies, J. Invest. Dermatol. 90:459). In the present invention, it is demonstrated that gp75 cDNA had approximately 90% identity with the derived amino acid and nucleotide sequences of a mouse gene that maps to the b (brown) locus. The brown locus is a site that determines coat color and influences the type of melanin synthesized, suggesting that gp75 may regulate or influence the type of melanin synthesized.

The fact that IgG antibodies in sera of a patient with metastatic melanoma have been shown to immunoprecipitate gp75 demonstrates that immunological tolerance against gp75 can be broken. This invention therefore provides expression vectors comprising gp75 cDNA for use as a vaccine against melanoma, whereby the amino acid sequences of peptides were determined from gp75 polypeptide, which was isolated and purified by the mouse monoclonal antibody TA99, and whereby cDNA clones were isolated by screening with oligonucleotides based on the peptide sequences.

b. Human Prostatic Specific Reductase.

U.S. Pat. No. 6,106,829, issued to He, et al. uses a human prostatic specific reductase polypeptide as a diagnostic marker for prostate cancer and as an agent to determine if the prostate cancer has metastasized. The patent also discloses antibodies specific to the prostatic specific reductase polypeptide that may be used to target prostate cancer cells and be used as part of a prostate cancer vaccine.

c. Telomerase

Another method for treating tumors currently being evaluated by medical researchers makes use of a substance called telomerase, an enzyme that tumor cells produce and require to remain alive, but which normal body cells (except for sperm and hematopoietic system) neither produce nor require. This unique property of telomerase has prompted attempts to develop a drug that will block the action of the enzyme sufficiently to either inhibit the growth of new tumor cells or cause the death of older ones. Telomerase is an example of a class of substances that are often referred to as being "tumor-specific" because they are needed and/or used by tumor cells in differentially larger amounts than by normal healthy cells of the body.

Telomeres, the protein-DNA structures physically located on the ends of the eukaryotic organisms, are required for chromosome stability and are involved in chromosomal organization within the nucleus (See e.g., Zakian, Science 270: 1601 [1995]; Blackburn and Gall, J. Mol. Biol., 120:33 [1978]; Oka et al., Gene 10:301 [1980]; and Klobutcher et al., Proc. Natl. Acad. Sci., 78:3015 [1981]). Telomeres are believed to be essential in such organisms as yeasts and probably most other eukaryotes, as they allow cells to distinguish intact from broken chromosomes, protect chromosomes from degradation, and act as substrates for novel replication mechanisms. Telomeres are generally replicated in a complex, cell cycle and developmentally regulated, manner by "telomerase," a telomere-specific DNA polymerase. However, telomerase-independent means for telomere maintenance have been described. In recent years, much attention has been focused on telomeres, as telomere loss has been associated with chromosomal changes such as those that occur in cancer and aging.

Importantly, telomere replication is regulated both by developmental and cell cycle factors. It has been hypothesized that aspects of telomere replication may act as signals in the cell cycle. For example, certain DNA structures of DNA-protein complex formations may act as a checkpoint to indicate that chromosomal replication has been completed (See e.g., Wellinger et al., Mol. Cell. Biol., 13:4057 [1993]). In addition, it has been observed that in humans, telomerase activity is not detectable in most somatic tissues, although it is detected in many tumors (Wellinger, supra). This telomere length may serve as a mitotic clock, which serves to limit the replication potential of cells in vivo and/or in vitro. What remains needed in the art is a method 25 to study the role of telomeres and their replication in normal as well as abnormal cells (i.e., cancerous cells). An understanding of telomerase and its function is needed in order to develop means for use of telomerase as a target for cancer therapy or anti-aging processes.

Despite the wide-ranging and expensive efforts expended in researching, developing and evaluating new treatments and cures for tumors and cancers, no truly significant advances or completely satisfactory treatments have thus far been achieved.

SUMMARY OF THE INVENTION

It is therefore an object of the present invention to provide a novel and effective treatment modality for both benign and malignant tumors. The treatment must avoid the disadvantages and dangers of the prior treatments discussed above, especially with respect to the use of radioactive substances and chemotherapy.

Another object of the present invention contemplates the ability to construct a vaccine that is universally effective against any proliferating tumor.

To achieve these objectives, a most preferred embodiment of this invention is a universal vaccine for treating tumors of any origin, having at least one telomerase reverse transcriptase (hTRT) peptide in an amount effective for initiating and enhancing a cytotoxic T lymphocyte (CTL) response against mammalian cancer cells in a physiologically acceptable carrier. Preferably, the telomerase peptide is modified to enhance binding to a major histocompatibility complex (MHC) molecule.

The MHC molecule may advantageously be a Class I human leucocyte antigen (HLA), for example, HLA-A2. Preferably, the hTRT peptide is a synthetic human telomerase reverse transcriptase peptide, but it may also be an effective synthetic homologue. Preferably, the peptide is from about 7 to about 15 amino acid residues in length, and most preferably, a 9mer. It may be effective either alone or in combination with other peptides.

The vaccine preparation described hereinabove may also comprise an adjuvant or facilitator. One highly preferred facilitator is an interleukin molecule. Also contemplated by this invention, is a synthetic hTRT peptide advantageously restricted by a Class I major histocompatibility complex (MHC) molecule.

Another object of the invention is a method for inducing and enhancing a CTL response against cancer cells. This method comprises harvesting mammalian blood leucocytes, pulsing the leucocytes with an effective amount of hTRT, and contacting cancer cells with an effective amount of pulsed leucocytes. This contacting may be accomplished in vitro or in vivo. The method, in its simplest form, can be used in vitro for determining whether a cancer patient has potential immunity against his tumor, and is a likely candidate for treatment.

Yet another object of this invention contemplates a method for targeting cytotoxic lymphocytes (CTL) to tumor cells by administering an effective amount of telomerase reverse transcriptase (TRT) peptide to a mammalian recipient, which amount is effective to attract CTL to the tumor cells. The recipient preferably is a cancer patient.

These objects and other aspects and attributes of the present invention will become increasingly clear upon reference to the following drawings and accompanying specification.

BRIEF DESCRIPTION OF THE DRAWINGS

FIG. 5. Human Telomerase Reverse Transcriptase (hTRT) sequence (SEQ ID NO:23) [from Nakamura et al., 1997]

DESCRIPTION OF THE PREFERRED EMBODIMENT

Figure 1A:
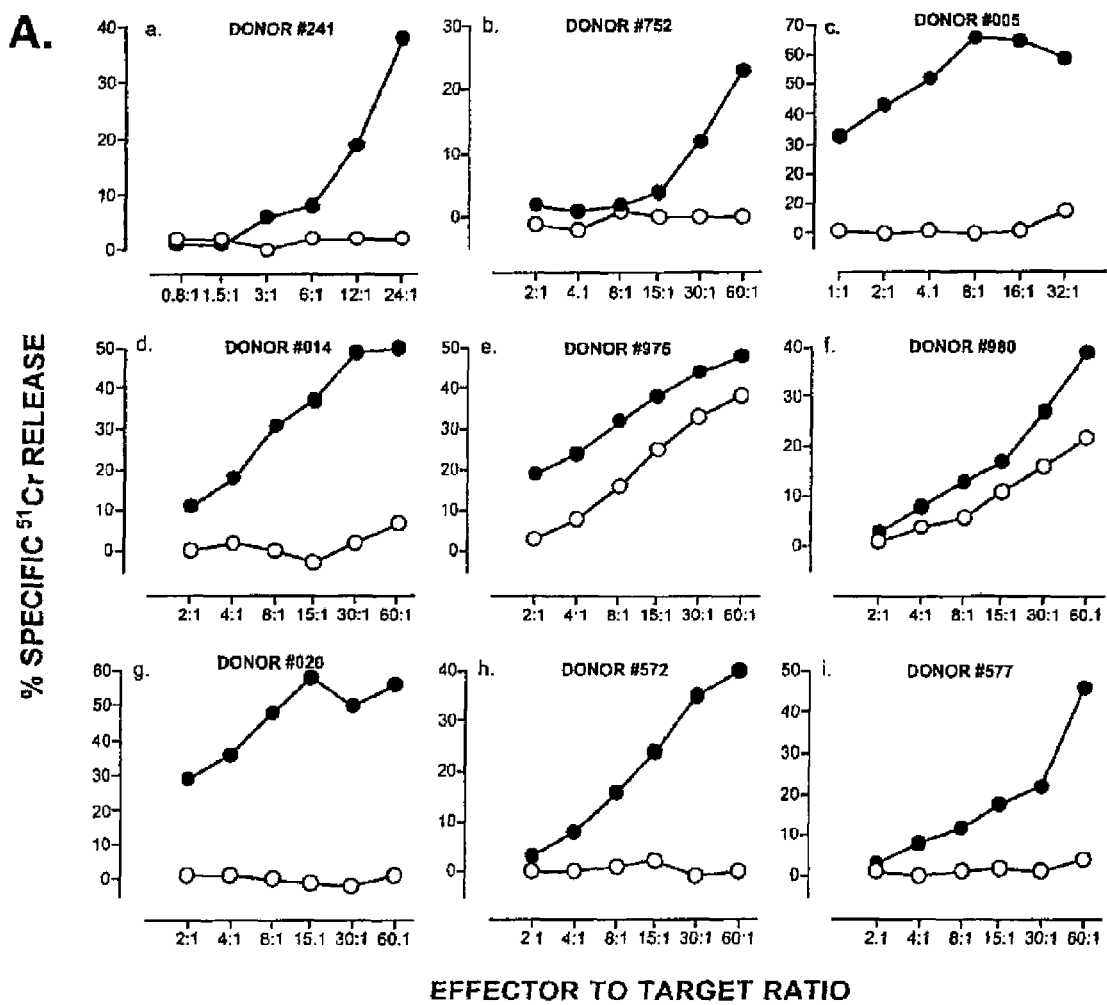
FIG. 1. Induction of CTL against hTRT in peripheral blood leucocytes (PBMC) from normal blood donors. T cells from HLA-A2+ individuals were stimulated by autologous PBMC pulsed with hTRT-derived synthetic peptides as detailed in the Material and Methods. (A). Results refer to effector cells from individual donors immunized in vitro against p540. Open circles define T2 cells and closed circles T2 cells pulsed with p540 as targets. (B). Results refer to effector cells from individual donors immunized in vitro against p865. Open diamonds define T2 cells and closed diamonds T2 cells pulsed with p865 as targets. Effector to target ratios are indicated on an individual basis. Percent cytotoxicity was calculated as specified in The Materials and Methods.

As used herein, the terms "telomerase" and "telomerase complex" refer to functional telomerase enzymes. It is intended that the terms encompass the complex of proteins found in telomerases. For example, the terms encompass the 123 kDa and 43 kDa telomerase protein subunits.

Telomerase is a ribonucleoprotein enzyme, which has been linked to malignant transformation in human cells. Telomerase activity is increased in the vast majority of human tumors making its gene product the first molecule common to all human tumors. The generation of endogenously-processed telomerase peptides bound to Class I major histocompatibility complex (MHC) molecules could therefore target cytotoxic T lymphocytes (CTL) to tumors of different origins. This could advance vaccine therapy against cancer provided that precursor CTL recognizing telomerase peptides in normal adults and cancer patients can be expanded through immunization. Applicant demonstrates here that the majority of normal individuals and patients with prostate cancer immunized in vitro against two HLA-A2.1 restricted peptides from telomerase reverse transcriptase (hTRT), develop hTRT specific CTL. This suggests the existence of precursor CTL for hTRT in the repertoire of normal individuals and in cancer patients. Most importantly, cancer patients' CTL specifically lysed a variety of HLA-A2+ cancer cell lines, demonstrating immunological recognition of endogenously-processed hTRT peptides. Moreover, in vivo immunization of HLA-A2.1 transgenic mice generated a specific CTL response against both hTRT peptides. Based on the induction of CTL responses in vitro and in vivo, and the susceptibility to lysis of tumor cells of various origins by hTRT CTL, Applicant suggests that hTRT could serve as a universal cancer vaccine for humans.

INTRODUCTION

Telomerase is a unique ribonucleoprotein that mediates RNA-dependent synthesis of telomeric DNA (1), the distal ends of eukaryotic chromosomes that stabilize the chromosomes during replication (2, 3). When activated, telomerase synthesizes telomeric DNA and compensates for its loss with each cell division (4). Since telomeres shorten progressively with successive cell divisions, telomere length is considered to mirror the replicative history of cell lineage (5) and cell population dynamics (6, 7). In mice, telomerase appears to play an essential role in the long-term viability of high-renewal organ systems such as the reproductive and haemopoietic systems (8).

Maintenance of a constant telomere length ensures chromosomal stability, prevents cells from aging, and confers immortality (9-11). Mice lacking telomerase RNA show that telomerase activation is a key event in malignant cell transformation (8, 12, 13). In humans, in vitro studies show that the long-term ectopic expression of telomerase reverse transcriptase (hTRT) in normal fibroblasts is sufficient for immortalization but not malignant transformation (14). However, the expression of hTRT in combination with two oncogenes (SV40 T antigen and Ras) promotes tumor transformation in normal human epithelial and fibroblast cell lines (15). These transformed cells form tumors in nude mice. Thus, although telomerase per se is not tumorigenic, it plays a direct role in oncogenesis by allowing pre-cancerous cells to proliferate continuously and become immortal. The PCR-based TRAP assay (16) reveals a striking correlation (>80%) between high telomerase activity and tumors of different histological origins and types (17, 18). In contrast, normal tissues display little or no telomerase activity (18, 19). Therefore, telomerase expression in tumors is much greater than HER2/neu and mutated P53, which range between 30% and 50% respectively (20, 21). From the foregoing, it is reasonable that expression of hTRT in cancer cells is a likely source of peptides that, upon association with major histocompatibility complex (MHC) Class I molecules, could target cytotoxic T lymphocytes (CTL) to cancer cells. An interesting analogy exists with HIV-1 reverse transcriptase, an enzyme similar to hTRT, which gives origin to peptide/MHC Class I complexes that target CTL responses to virus infected cells (22). Thus, since high telomerase activity is widespread among human tumors, hTRT could serve as a universal tumor antigen for immunotherapy and vaccine approaches.

hTRT is encoded in the genome and is in all respects a self antigen. Consequently, CD8+ T lymphocytes with a receptor for MHC/hTRT peptide complexes are expected to be eliminated during thymic negative selection, reducing the potential precursor T cell repertoire and imposing limitations on their expansion upon encounter with tumor cells in adult life. Additionally, stimulation by antigen in the absence of a second signal induces clonal anergy (23), further hampering the potential repertoire. The extent to which these events affect the normal adult repertoire, and whether or not exposure to hTRT during cancer formation has any adverse effect on the ability of cancer patients to respond, is not known. Because answering these questions is relevant to future strategies of immune intervention targeted at hTRT, the ability of normal individuals and cancer patients to mount a CTL response in vitro against two hTRT peptides restricted by the HLA-A2 allele was analyzed.

Materials and Methods

Example 1

Synthetic Peptides hTRT synthetic peptides p540 (540ILAKFLHWL548, SEQ ID NO:1), p865 (865RLVDDFLLV873, SEQ ID NO:2) and MART-1 (27AAGIGILTV35, SEQ ID NO:3) were purchased from the Biopolymer Synthesis Center (CalTech, Pasadena, Calif.). Synthetic peptides 128TPPAYRPP-NAPIL140 (SEQ ID NO:4) of the hepatitis B core antigen (HBVc), 571YLSGANLNL579 (SEQ ID NO:5) of carcinoembryonic antigen (CEA), 476VLYRYGSFSV486 (SEQ ID NO:6) of melanoma antigen gp100, 476ILKEPVHGV484 (SEQ ID NO:7) of HIV-1 reverse transcriptase were purchased from Neosystem (Strasburg, France).

Human Blood Cells

Buffy coats from normal donors were purchased from the San Diego Blood Bank. HLA-A2+ individuals were selected by FACS screening using monoclonal antibody BB7.2. Prostate cancer patients were recruited through the Division of Urology (University of California, San Diego). Blood from these patients was obtained by venipuncture. HLA-A2+ individuals were selected by FACS screening using monoclonal antibody BB7.2. Blood collection and experiments were performed in accordance with an approved IRB.

Tumor Cell Lines

T2 cells were a kind gift of Dr. Peter Creswell (Yale University). Melanoma cell lines 624 and 1351 were the kind gift of Dr. John Wunderlich (National Cancer Institute, Bethesda, Md.). Prostate cancer cell lines LnCap and PC-3 were the kind gift from Dr. Antonella Vitiello (PRI Johnson, La Jolla Calif.). Breast, colon and lung tumor cell lines were obtained from ATCC, Rockville, Md.

Example 2

In Vitro Immunization

PBMC were separated by centrifugation on Ficoll-Hypaque gradients and plated in 24-well plates at $5 \times 10^5$ cells/ml/well in RPMI-1640 supplemented with 10% human AB+ serum, L-glutamine and antibiotics (CM). Autologous PBMC (stimulators) were pulsed with hTRT synthetic peptides p540 or p865 (10 µg/ml) for 3 hours at 37° C. Cells were then irradiated at 5000 rads, washed once, and added to the responder cells at a responder: stimulator ratio ranging between 1:1 and 1:4. The next day, 12 IU/ml IL-2 (Chiron Co., Emeryville, Calif.) and 30 IU/ml IL-7 (R&D Systems, Minneapolis, Minn.) were added to the cultures. Lymphocytes were re-stimulated weekly with peptide-pulsed autologous adherent cells as follows. First, autologous PBMC were incubated with hTRT peptide (10 µg/ml) for 3 hours at 37° C. Non-adherent cells were then removed by a gentle wash and the adherent cells were incubated with fresh medium containing the hTRT peptide (10 µg/m) for an additional 3 hours at 37° C. Second, responder cells from a previous stimulation cycle were harvested, washed and added to the peptide-pulsed adherent cells at a concentration of $5 \times 10^5$ cells/ml (2 ml/well) in medium without peptide. Recombinant IL-2 and IL-7 were added to the cultures on the next day.

Example 3

In Vivo Immunization

HHD mice were immunized subcutaneously at the base of the tail with 100 µg of individual hTRT peptide emulsified in incomplete Freunds' adjuvant (IFA). Half of the mice were immunized with the hTRT peptide and 140 µg of the helper peptide TPPAYRPPNAPIL (SEQ ID NO:4), which corresponds to residues 128-140 of the hepatitis B core antigen (HBVc) (25).

Example 4

HLA-A2.1 Binding/Stabilization Assay

The relative avidity was measured as previously described (25). Briefly, T2 cells were incubated overnight at 37° C. in RPMI supplemented with human β2-microglobulin (100 ng/ml) (Sigma, St. Louis, Mo.) in the absence (negative control) or presence of the test peptide or the reference peptide 476ILKEPVHGV484 (SEQ ID NO:7) of HIV-1 reverse transcriptase at various final peptide concentrations (0.1-100 µM). Cells were incubated with Brefeldin A (0.5 µg/ml) for one hour and subsequently stained with a saturating concentration of monoclonal antibody BB7.2 for 30 minutes at +4° C. followed by washing and a second incubation with a goat antibody to mouse Ig (Fab')2 conjugated to FITC (Caltag, South San Francisco). Cells were then washed, fixed with 1% paraformaldehyde and analyzed in a FACs Calibur cytofluorimeter (Becton & Dickinson, San Jose, Calif.). The mean fluorescence intensity of each concentration minus that of cells without peptide was used as an estimate of peptide binding. Results are expressed as values of RA, which is the ratio of the concentration of test peptide necessary to reach 20% of the maximal binding by the reference peptide over that of the reference peptide so that the lower the value the stronger the binding. Dissociation of the test peptide from the HLA-A2.1 molecule reflects the half-life of fluorescence intensity of the peptide/MHC complex over time. The half-life of the complex (DC50) refers to the time (hours) required for a 50% reduction of the TO mean fluorescence intensity (25). Synthetic peptides 571YLSGANLNL579 (SEQ ID NO:5) of carcinoembryonic antigen (CEA) and 476VLYRYGSFSV486 (SEQ ID NO:6) of melanoma antigen gp100 were used as internal controls to account for intertests variability and for consistency with previously reported RA and DC50 measures (25).

Example 5

Figure 1B:
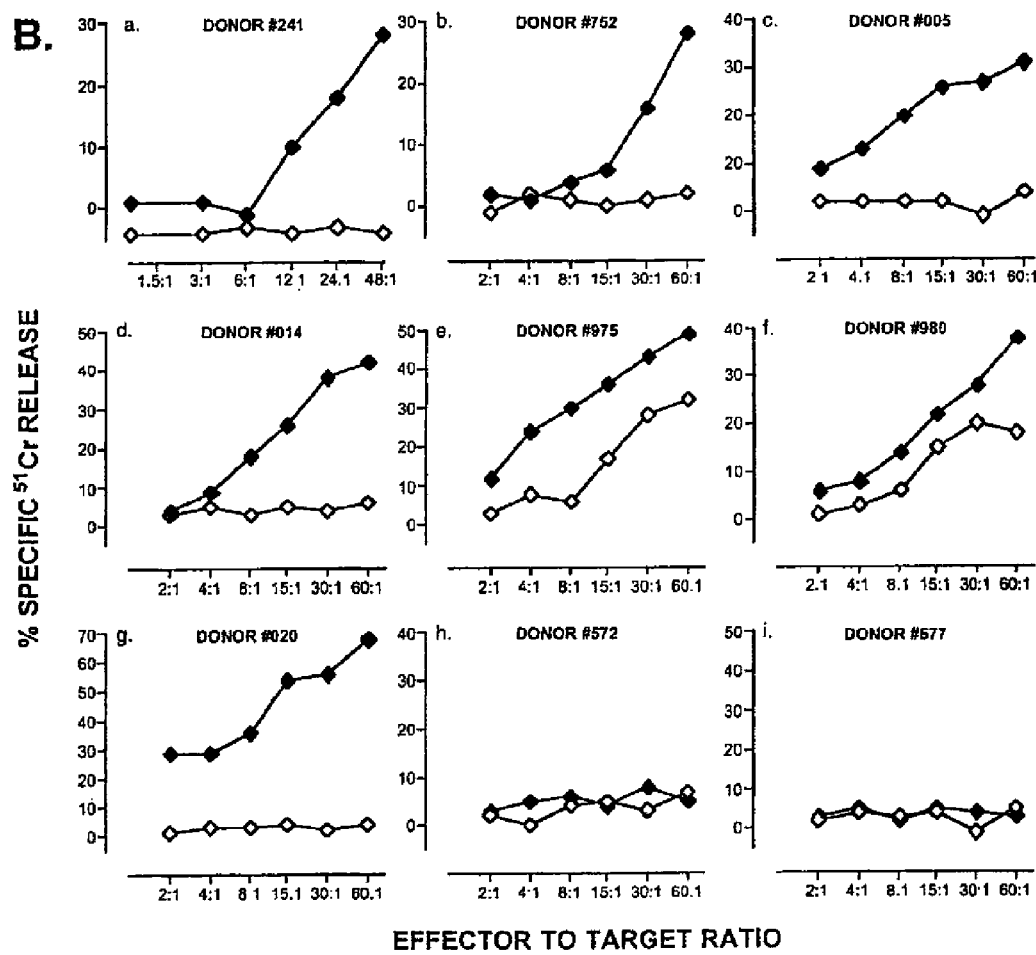

Cytotoxicity Assay (a) The induction of CTL in human PBMC was monitored in a conventional $^{51}$Cr-release assay. Briefly, peptide-pulsed TAP-/HLA-A2.1+ human T2 cells were incubated with 10 µg of hTRT peptides or with the MART-1 control peptide for 90 minutes during labeling with $^{51}$Cr. After washing, the target cells were added to serially diluted effectors in 96-well microplates. After a 6 hour incubation period at 37° C., supernatants were harvested and counted in a Trilux Betaplate counter (Wallac, Turku, Finland). Results are expressed as the percentage (%) of specific lysis and determined as follows: [(experimental cpm−spontaneous cpm)/(maximum cpm spontaneous cpm)]×100. (b) The induction of CTL in HHD mice was assessed as follows. Spleen cells were harvested 7 days after immunization and were restimulated in vitro with the corresponding hTRT peptide and LPS (25 µg/ml)-stimulated irradiated (5000 rads) syngeneic spleen cells. After six days of culture the cells were harvested and tested for their ability to lyse HHD-transfected/TAP-RMA-cells in a 4 hour $^{51}$Cr-release assay (25). Specific lysis was calculated as indicated in the legend of FIG. 1. Values refer to maximal cytotoxicity measured for individual responder mice at an effector to target ratio of 60:1.

Results

Example 6

Identification and Analysis of HLA-A2.1-Restricted hTRT Peptides

The amino acid sequence of hTRT (locus AF015950) (19) was analyzed for 9mer peptide sequences containing known binding motifs for the HLA-A2.1 molecule [52; 35; 60], a subtype encompassing 95% of HLA-A2 allele, which is expressed in about 50% of the Caucasian population (26-28). Peptides were identified by reverse genetics based on canonical anchor residues for HLA-A2.1 (29), and by using the software of the Bioinformatics & Molecular Analysis Section (NIH) website bimas.dcrt.nih.gov/molbio/hla_bind/index.html, which ranks 9mer peptides on a predicted half-time dissociation coefficient from HLA Class I molecules (30). From an initial panel of 30 candidate peptides Applicant retained two sequences, 540ILAKFLHWL548 (SEQ ID NO: 1) and 865RLVDDFLLV873 (SEQ ID NO:2), denoted hereunder as p540 and p865.

Since the immunogenicity of MHC Class I-restricted peptides reflects to some degree their binding and stabilizing capacity for MHC Class I molecules (31-33) Applicant sought direct proof of the strength of interaction between the two hTRT peptides and the HLA-A2.1 molecule in a conventional binding/stabilization assay that uses the antigen-transporting deficient (TAP-) HLA-A2.1+ human T2 cells. The relative avidity (RA) calculated in reference to 476ILKEPVHGV484 (SEQ ID NO:7) of HIV-1 reverse transcriptase, a canonical high binder peptide (25), was 2.9 and 2.5 for p540 and p865, respectively (Table I). The stability of each peptide bound to HLA-A2.1 was measured as the half-life of the complex

TABLE I

| Peptide origin/ designation | Sequence | Relative Avidity (RA)[a] | DC50[b] |
|---|---|---|---|
| hTRT p540 | ILAKFLHWL (SEQ ID NO:1) | 2.9 | 4-6 |
| hTRT p865 | RLVDDFLLV (SEQ ID NO:2) | 2.5 | 2-4 |
| CEA p571[c] | YLSGANLNL (SEQ ID NO:5) | 3 | >10 |
| gp100 p476[d] | VLYRYGSFSV (SEQ ID NO:6) | 9 | 4-6 | a. The relative avidity of hTRT peptides was measured relative to the reference peptide ILKEPVHGV (SEQ ID NO:7) at a final peptide concentration of 0.1-100 mM.
b. DC50 refers to the time required for a 50% reduction in mean fluorescence intensity.
c. Peptides of human carcinoembryonic antigen (CEA) (p571) and human melanoma antigen gp100 (p476) were used as internal controls for comparison with previously reported values[33]. (DC50) and was in the order of 4-6 hours for p540 and 2-4 hours for p865, respectively. Collectively, these measurements indicate that both hTRT peptides are excellent binders to HLA-A2.1 albeit p865 has a faster dissociation rate.

Example 7

CTL Response Against hTRT in Normal Human Individuals

The presence of precursor T cells for both hTRT peptides and their expansion upon antigen stimulation were tested using peripheral blood lymphocytes (PBMC) of 10 HLA-A2+ normal blood donors in an in vitro immunization assay. Nine out of 10 individuals responded to immunization generating T cells that lysed peptide-pulsed T2 cells as targets starting from the third round of peptide stimulation. All nine responders generated CTL specific for p540 and seven responded against p865 (FIGS. 1, A and B). The values of maximal lysis varied from individual to individual and ranged between 28-68% and 20-68%, respectively. In two instances (donor 975 and 980) there was a lower but measurable non-specific lysis, possibly due to contaminant NK cells. Thus, by random testing of normal HLA-A2+ individuals, it was clearly established that both hTRT peptides are immunogenic, implying that precursor CTL for hTRT are present in the peripheral adult repertoire.

Example 8

CTL Response Against hTRT in Cancer Patients

Figure 2A:
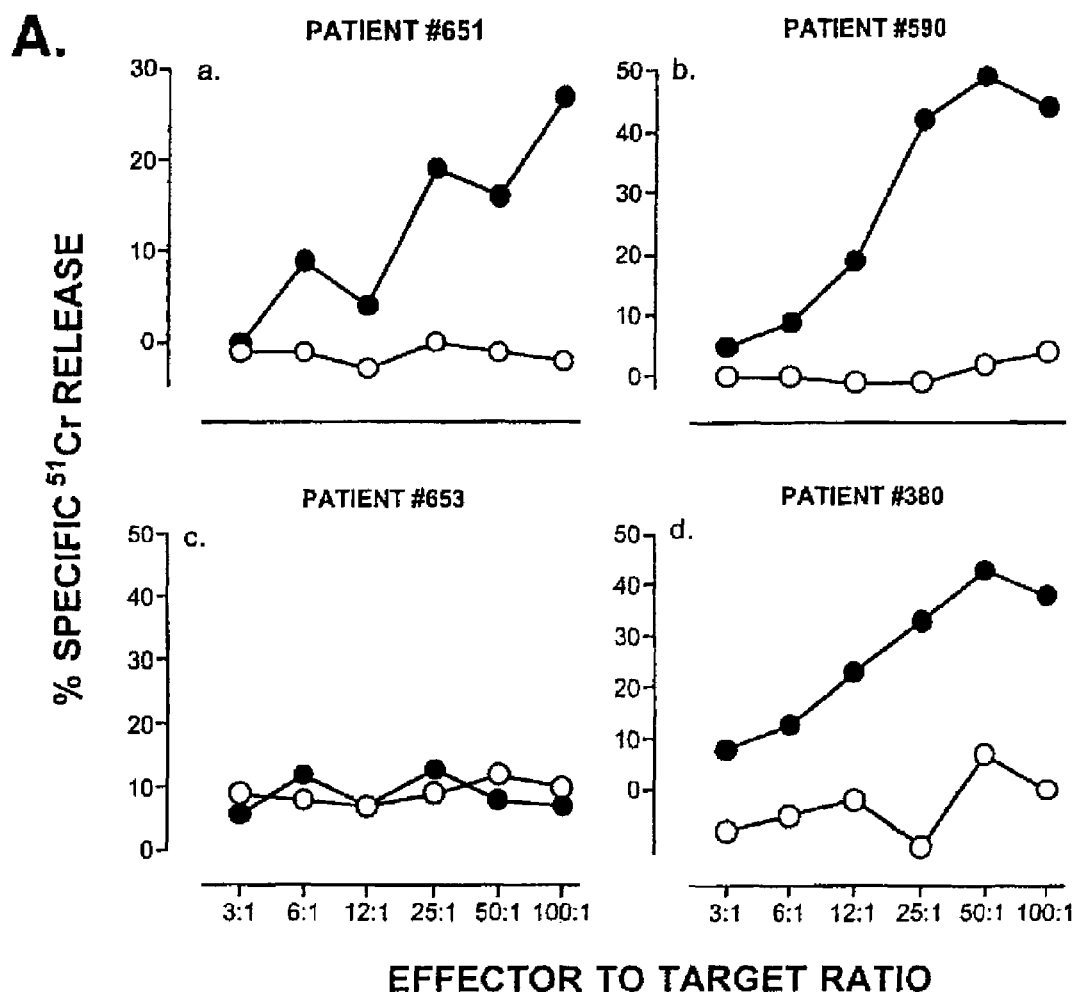
FIG. 2. Induction of CTL against hTRT in PBMC from prostate cancer patients. (A). Results refer to effector cells from individual patients immunized against p540. Values refer to cells tested after three rounds of in vitro stimulation. Open circles define T2 cells and closed circles T2 cells pulsed with p540 as targets. (B). Results refer to effector cells from individual patients immunized against p865. Open diamonds define T2 cells and closed diamonds T2 cells pulsed with p865 as targets. Effector to target ratios are indicated on an individual basis. (C). Results refer to effector cells from individual patients immunized in vitro against p540 (circles) or p865 (diamonds). Open symbols define the HLA-A2-PC-3 prostate cancer cell line as a target. Closed symbols define the HLA-A2+ prostate cancer cell line LnCap as a target. Percent cytotoxicity was calculated as specified in the Materials and Methods section.
Figure 2B:
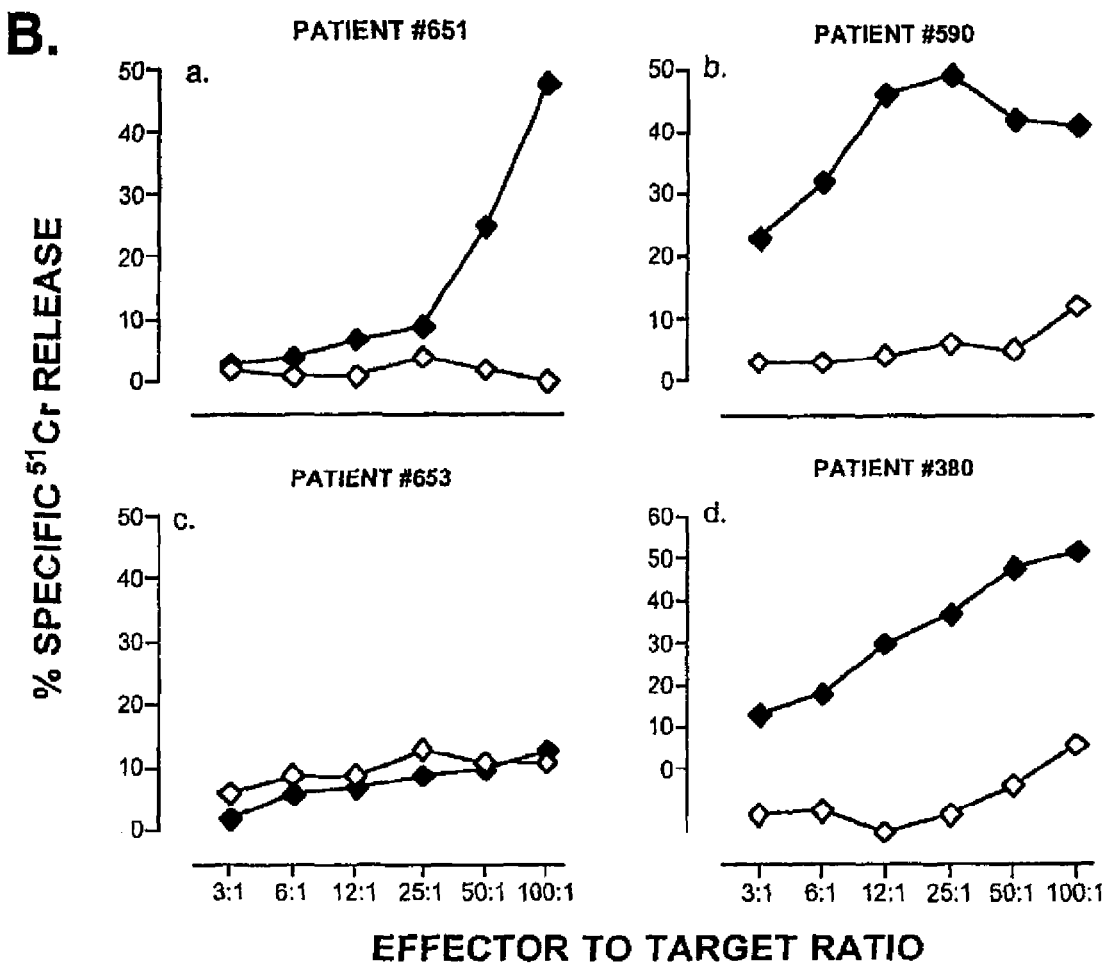
Figure 2C:
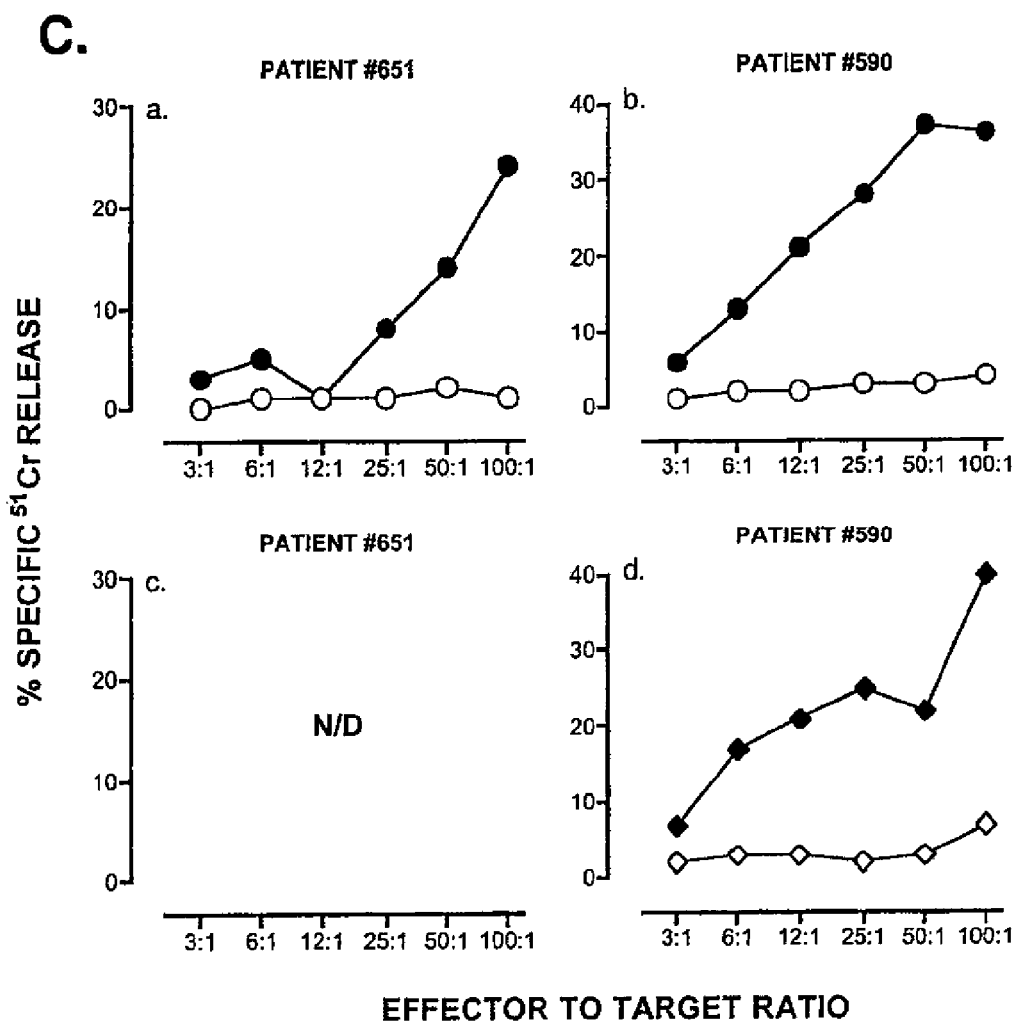

Whether or not CTL against hTRT could also be induced in cancer patients was studied in four HLA-A2.1+ individuals with clinical and histological diagnosis of prostate cancer. All four patients were refractory to hormonal therapy, three had metastases and none had prostatectomy. In prostate cancer, the most common cause of cancer in men, high hTRT expression has been documented in 84% of cases (34). Marked lysis of peptide-pulsed T2 cells was observed in 3 out of 4 individuals after three rounds of in vitro stimulation (FIGS. 2, A and B). Both peptides yielded comparable CTL responses in all three individuals with maximal lysis ranging between 27-49% and 48-52%, respectively. CTL against both peptides lysed LnCap, a HLA-A2.1+ prostate cancer cell line, with maximal lysis ranging between 24-36% for p540 and 12-40% for p865. Prostate cancer cell line PC-3, which is HLA-A2.1−, was used as control and was not lysed (FIG. 2, C).

Both prostate cancer cell lines tested positive for hTRT by the TRAPeze (telomerase detection assay; INTERGEN) (not shown), suggesting that the CTL generated against the synthetic peptides might lyse cancer cells by recognizing hTRT-peptide/MHC Class I complex at the surface of cancer cells.

Figure 3A:
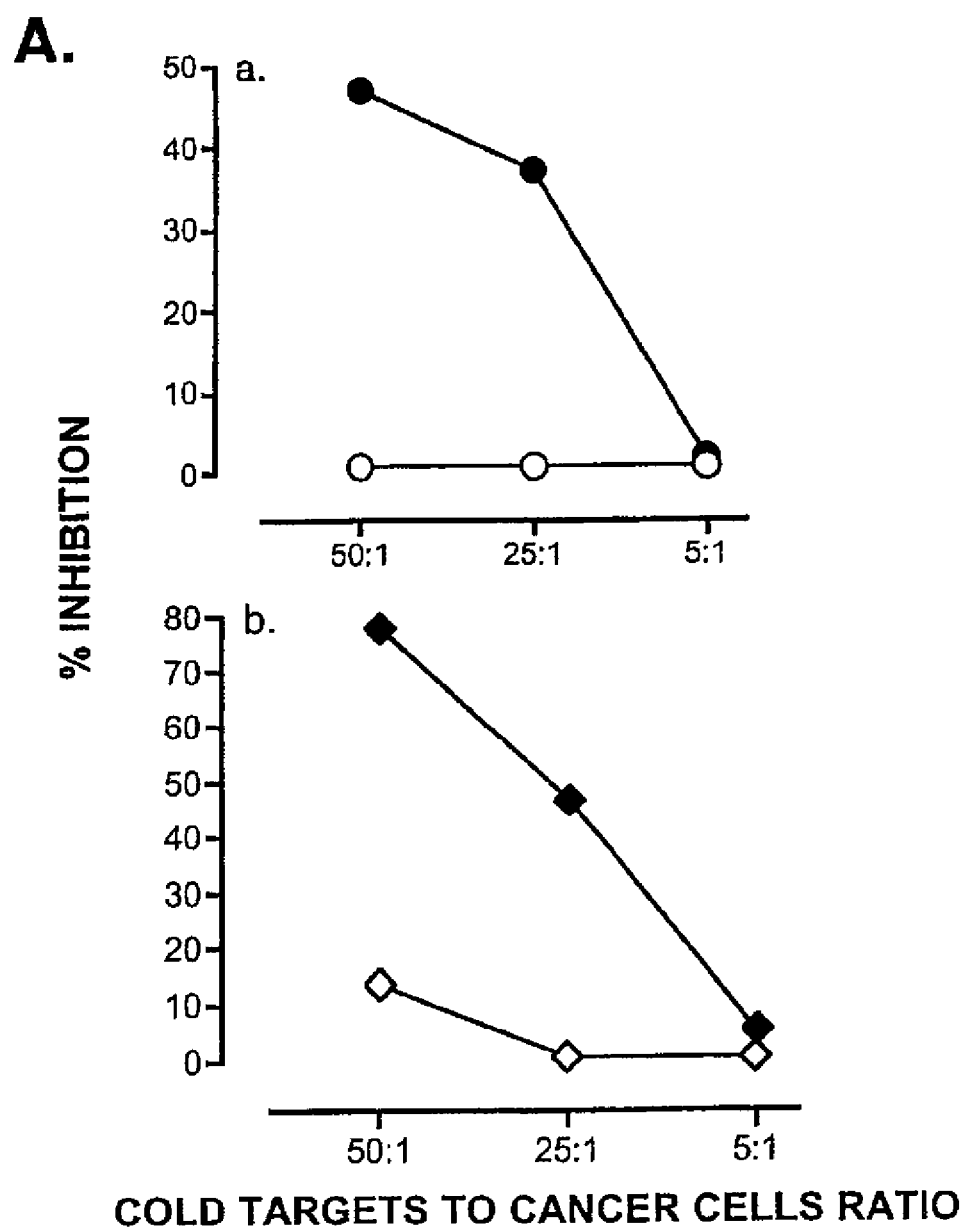
FIG. 3. Molecular specificity of target recognition by CTL generated against hTRT peptides. (A). Cold target inhibition. $^{51}$Cr-labeled LnCap cells ($5 \times 10^4$ cells/ml) were mixed with T2 cells (open symbols) or T2 cells pulsed with p540 (closed circles) or p865 (closed diamond) (1 μg/ml) at a cold:hot target cell ratio of 5:1, 25:1 and 50:1. Patients' CTL lines 380.540.1 and 380.865.1 generated against p540 and p865, respectively, were added at an E:T ratio of 50:1. (B) Lysis of T2 cells pulsed with irrelevant HLA-A2 binding peptides. Results refer to lysis by patients' (#651) CTL generated against p540 (panel a) or p865 (panel b), and patients' (#380) CTL generated against p540 (panel c) or p865 (panel d). Closed symbols define T2 cells pulsed with p540 (circles), p865 (diamonds) and MART-1 peptide (triangles). Open circles refer to non-pulsed T2 cells. Percent cytotoxicity was calculated as specified in The Material and Methods.
Figure 3B:
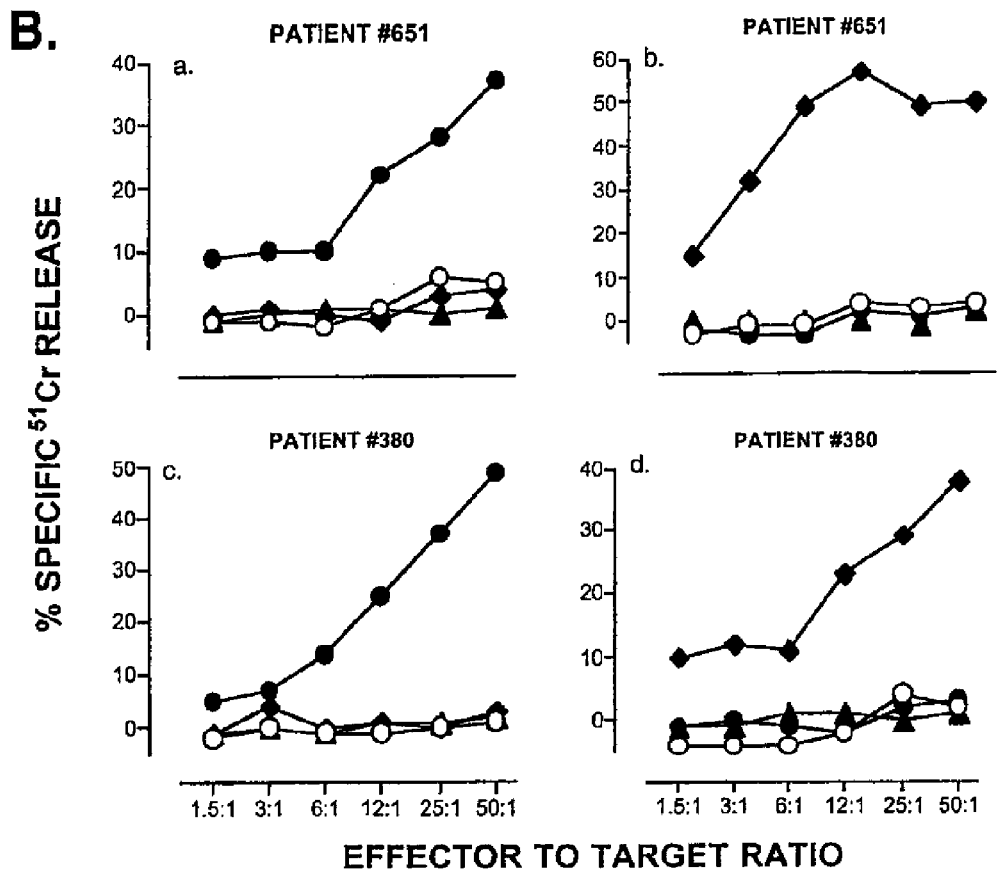
Figure 4:
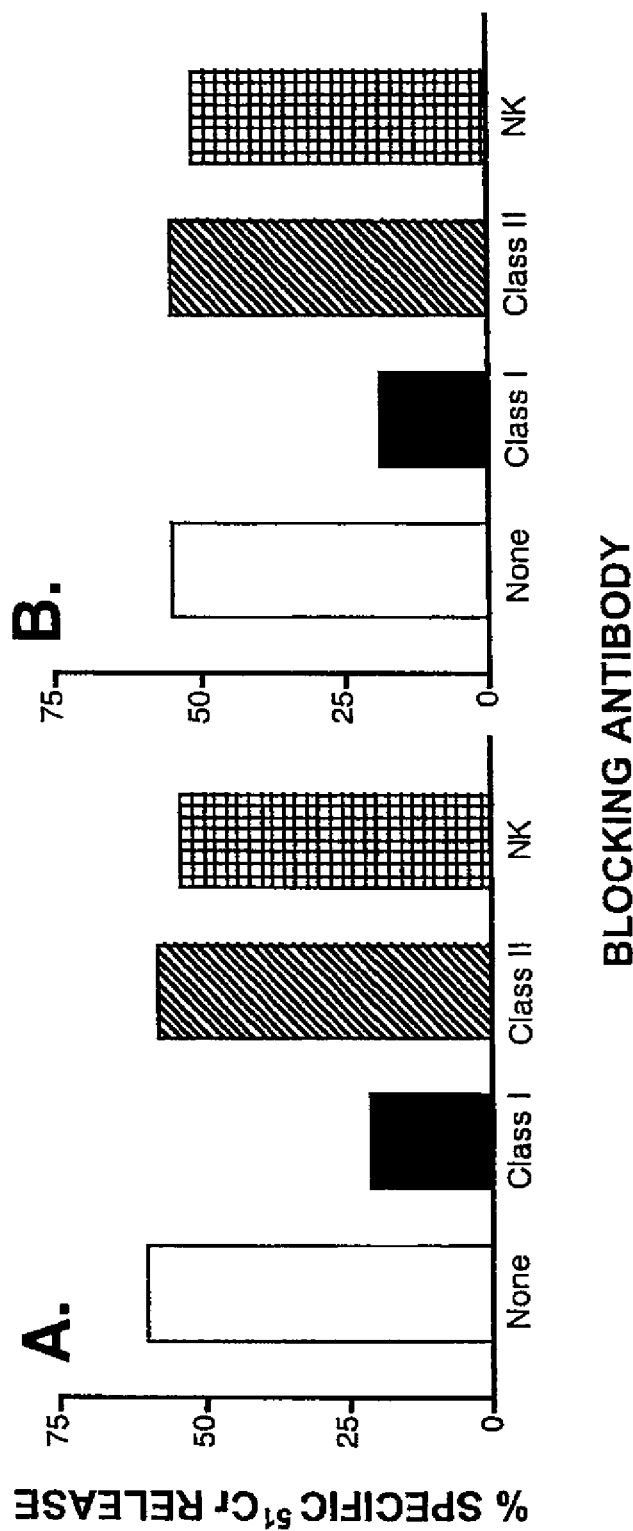
FIG. 4. Prostate cancer patients' CTL against hTRT are MHC Class I restricted. Patient CTL lines 380.540.1 and 380.865.1 were tested in a $^{51}$Cr-release assay using as targets T2 cells pulsed with p540 (A) or p865 (B). The following inhibitory antibodies were used: murine monoclonal antibody BB7.2 (IgG2b) against MHC 15 Class I, murine monoclonal antibody Q5/13 (IgG2a) against HLA-DR, and the engineered antibody 1RGD3 that blocks NK cell function.

Cold target competition experiments were performed in an attempt to understand if lysis of the LnCap tumor cell line was specific for endogenously processed hTRT peptides. In these experiments the lysis of LnCap cells by CTL from a prostate cancer patient was competed for by T2 cells pulsed in vitro with p540 or p865 (10 μg/ml). Peptide-loaded T2 cells caused a dose-dependent inhibition of lysis of LnCap cells in both peptide combinations (FIG. 3, A). Applicant further assessed the specificity of the CTL generated against each one of the two hTRT peptides by testing them on T2 targets pulsed with irrelevant HLA-A2 binding peptides. Neither T2 cells pulsed with peptide 27AAGIGILTV35 (SEQ ID NO:3) from the melanoma antigen MART-1 nor T2 cells pulsed with a non-homologous hTRT peptide were lysed (FIG. 3, B). Collectively, these studies show that 1) patients' CTL are specific for the hTRT peptide used to induce them, and 2) lysis of prostate cancer cells is mediated by, and is specific for, endogenously-processed hTRT peptides complexed with HLA-A2.1 molecules, suggesting chemical identity between naturally processed peptides on tumor cells and the synthetic peptides used for immunization. Formal validation will require elution of peptides from tumor cells and their analysis by tandem mass spectrometry (35). Studies on MHC restriction were performed using blocking antibodies. Lysis of peptide-pulsed T2 cells by CTL lines generated from a prostate cancer patient was inhibited by the anti-MHC Class I monoclonal antibody BB7.2 in both peptide combinations (FIG. 3), but not by the anti-MHC Class II monoclonal antibody Q5/13 (36) nor by transfectoma antibody 1RGD3 that blocks NK cells (37). By two-color FACS analysis, the phenotype of T cells proliferating after three rounds of in vitro stimulation with hTRT peptide was CD3+ (78%), CD8+ (37%), CD4+ (36%) and CD16/56 (6%). Collectively, these experiments confirm that effector T cells generated by in vitro immunization are MHC Class I-restricted (CD8+) T cells which do not possess NK activity.

hTRT is expressed in normal cells such as circulating B and T cells, germinal center B cells, thymocytes and CD34+ progenitor hemopoietic cells (6, 7, 38). This implies that CTL generated against hTRT peptides could engender an autoimmune attack on normal cells. To this end, Applicant verified whether cancer patients' CTL would lyse HLA-A2+ CD34+ cells. Neither CTL against p540 nor those against p865 induced any lysis over a wide range of effector to target (E:T) ratios (not shown). Thus, at least with respect to hemopoietic stem cells an autoimmune attack appears unlikely. This is consistent with the fact that activated T cells were not lysed by hTRT CTL in culture.

Example 9

CTL Response Against hTRT in HLA-A2.1-Transgenic Mice

Whether peptides can serve as immunogens in vivo and elicit a CTL response depends on a variety of factors such as the mode of immunization, suitable activation of antigen presenting cells, the frequency of precursor cells, and binding and stabilization of MHC Class I molecules by peptide. In this study Applicant demonstrated (Table I) that both peptides bind to HLA-A2.1 with a RA<3 but possess different dissociation rates. In either case Applicant was able to generate CTL responses in vitro from PBMC of normal blood donors as well as prostate cancer patients. Therefore, a reasonable expectation would be that they may also be immunogenic in vivo. To test this possibility Applicant immunized H-2Db−/−, β2m−/−, HLA-A2.1+ monochain transgenic HHD mice (39). In these mice the peripheral CD8+ T cell repertoire is essentially educated on the transgenic human molecule. Therefore, HHD mice are an excellent tool to assess at the pre-clinical level the ability of individual peptides to induce HLA-A2.1 restricted CTL responses in vivo (25).

Both p540 and p865 were able to induce specific CTL responses (Table II) although differences were noted. In fact, p540 induced CTL whether alone or in combination with a helper peptide (66 vs. 80% responders). In contrast, a high (70%) response against p865 was obtained only when its immunogenicity was increased by association with the helper peptide. The different immunogenicity of the two hTRT peptides was also reflected by the magnitude of individual responses (55.8±9.4 vs. 20±11.5% lysis) against p540 and p865 with helper peptide, respectively. This is consistent with the observation that two normal blood donors responded to immunization against p540 but failed to respond against p865 (FIG. 1). Thus, there is an overall correlation between the results of binding/stabilization of the HLA-A2.1 molecule, the results of immunogenicity in vitro of human PBMC, and the response in vivo in HHD mice. Finally, to exclude the development of untoward autoimmunity HHD mice immunized against hTRT peptides were monitored with respect to the number of circulating B lymphocytes. Using a dual stain (B220 and anti-Ig) FACS analysis Applicant found no decrease in circulating B cells in immunized mice when compared to normal HHD mice (not shown). Furthermore, no enlarged mesenteric lymph nodes nor cellular infiltrates in the liver were noticed after immunization (not shown).

Example 10

Cancer Patients' CTL Kill Tumor Cells of Various Origins and Types

Because CTL generated against p540 and p865 recognize naturally-processed hTRT peptides on LnCap prostate cancer cells and hTRT activity is expressed at high levels in the

TABLE II

| INDUCTION OF CTL AGAINST HTRT IN HLA-A2.1 TRANSGENIC MICE | | | | |
| --- | --- | --- | --- | --- |
| Group | hTRT Peptide | Helper Peptide | No. Responders | Percent lysis |
| I | 5401LAKFLHWL548 (SEQ ID NO:1) | − | 10/15 (66%) | (35, 21, 34, 42, 56, 21, 12, 35, 42, 16) |
| II | 5401LAKFLHWL548 (SEQ ID NO:1) | + | 8/10 (80%) | (45, 56, 62, 64, 65, 45, 65, 45) |

TABLE II-continued

INDUCTION OF CTL AGAINST HTRT IN HLA-A2.1 TRANSGENIC MICE

| Group | hTRT Peptide | Helper Peptide | No. Responders | Percent lysis |
|---|---|---|---|---|
| III | 865RLVDDFLLV873 (SEQ ID NO:2) | − | 3/15 (20%) | (25, 12, 15) |
| IV | 865RLVDDFLLV873 (SEQ ID NO:2) | + | 7/10 (70%) | (25, 32, 35, 12, 16, 18, 2 1) | a. HHD mice were immunized by a subcutaneous injection of 100 µg of hTRT peptide emulsified in incomplete Freunds adjuvant (IFA). In groups 2 and 4 the hTRT peptide was administered together with 140 µg of the helper peptide TPPAYRPPNAPIL (SEQ ID NO:4) (25).
b. Values of cytotoxicity refer to individual responder mice. Spleen-derived CTL were harvested 7 days after immunization and then cultured for six days with the homologous hTRT peptide. Values refer to maximal cytotoxicity at an effector to target ratio of 60:1.

vast majority of human cancers, recognition of hTRT-derived peptides by CTL could mediate killing of a wide variety of cancer types. CTL lines from a prostate cancer patient were used in a $^{51}$Cr-release assay to assess lysis of HLA-A2+ tumor cell lines of breast, colon, lung, and melanoma origin as targets. By the TRAPeze assay all these cell lines were hTRT positive. Peptide-pulsed T2 cells and LnCap prostate cancer cell line served as positive controls (Table III). All cell lines but the SW480 colon cell line were lysed by CTL generated against p540 (range lysis 39-48%). On the other hand, all cell lines but the H69 lung cell line were lysed by CTL generated against p865 (range lysis 37-41%). The cytotoxic activity was dependent on expression of the HLA-A2 molecule since tumor-matched cell lines of a different HLA type were not lysed. Collectively, these data indicate that hTRT peptides such as p540 and p865 are naturally-processed in a variety of tumor cell types.

The antigen-recognition activity of T cells is intimately linked with recognition of MHC (HLA in humans) molecules. This complex is located on chromosome 6, and encompasses nearly 200 genes encoding for MHC class I and class II among others. The initial discovery is in relation to the HLA-A2 allele, which is expressed in about 50% of the Caucasian population (56). About 95% of HLA-A2+ white individuals express the HLA-A2.1 subtype (53).

The majority of peptides bound to MHC class I molecules have a restricted size of 9±1 amino acids and require free N- and C-terminal ends (52; 59; 61). In addition to a specific size, different class I molecules appear to require a specific combination of usually two main anchor residues within their peptide ligands (52; 59). In the case of the human allele HLA-A2.1, these anchor residues have been described as leucine (L) at position 2 and L or valine (V) at the C-terminal end (52). More recently, Ruppert et al. found that a "canonical" A2.1 motif could be defined as L or M (methionine) at position 2 and L, V, or I (isoleucine) at position 9 (60).

Additional criteria were used to refine the selection process. Each of the non-anchor residues (position 1, 3, 4, 5, 6, 7, 8) has significant effect of the A2.1 binding (60). More specifically, some amino acids at position 1, 3, 6, 7, and 8 virtually abolish A2.1 binding capacity of peptides (60). Therefore, Applicant excluded all peptides with the following amino acids at the position specified: D (aspartate) and P (proline) at position 1; K (lysine) at position 3; R (arginine) or G (glycine) at position 6; and E (glutamate) at position 7 or 8. Through this selection Applicant excluded 12 and retained 27 peptides. By taking into account the frequency of each amino acid in each of the non-anchor positions for many 9mer peptides (60) Applicant defined a more accurate A2.1 binders and 10 out of the 27 peptides (Table IV):

TABLE III

| | | | | Percent Lysis[c] | |
|---|---|---|---|---|---|
| Cell Target | Cell Origin | HTRT Expression[a] | HLA-A2[b] | CTL p540[d] | CTL 865[d] |
| T2 + peptide | | ND | Pos. | 59 | 48 |
| T2 | | ND | Pos. | 11 | 4 |
| MCF7 | Breast | Pos. | Pos. | 39 | 41 |
| SKBR3 | | Pos. | Neg. | 7 | 9 |
| SW480 | Colon | Pos. | Pos. | 12 | 37 |
| HCT011 | | Pos. | Neg. | 9 | 6 |
| H69 | Lung | Pos. | Pos. | 41 | 9 |
| H146 | | Pos. | Neg. | 11 | 5 |
| 624 | Melanoma | Pos. | Pos. | 48 | 39 |
| 1351 | | Pos. | Neg. | 12 | 6 |
| Lncap | Prostate | Pos. | Pos. | 44 | 41 |
| Pc3 | | Pos. | Neg. | 9 | 5 |

[a]hTRT expression of the tumor cells was determined by a PCR-based assay (TRAPezeR, Intergen).
[b]Expression of HLA-A2 was measured by flow cytometry using the monoclonal antibody BB7.2.
[c]Cellular cytotoxicity was measured in a $^{51}$Cr-release assay at an effector to target ratio of 50:1. All tumor cell lines were incubated with 100 IU/ml of recombinant IFN-γ for 48 hours before the $^{51}$Cr-release assay.
[d]Patient's CTL lines 380.540.1 and 380.865.1 were generated by immunization with p540 and p865, respectively.

TABLE IV

HTRT-DERIVED HLA-A2.1-RESTRICTED PEPTIDES

| Anchor Position L at position 2 V at position 9 | SEQ ID NO: | Anchor Position L at position 2 L or I at position 9 | SEQ ID NO: | Anchor Position M at position 2 V, L or I at position 9 | SEQ ID NO: |
|---|---|---|---|---|---|
| 152LLARCALFV160 | 8 | 96VLAFGFALL104 | 9 | 812FMCHHAVRI820 | 17 |
| 865RLVDDFLLV873 | 2 | 675LLGASVLGL683 | 10 | | |
| | | 724RLTEVIASI732 | 11 | | |
| | | 797SLNEASSGL805 | 12 | | |

TABLE IV-continued

HTRT-DERIVED HLA-A2.1-RESTRICTED PEPTIDES

| Anchor Position L at position 2 V at position 9 | SEQ ID NO: | Anchor Position L at position 2 L or I at position 9 | SEQ ID NO: | Anchor Position M at position 2 V, L or I at position 9 | SEQ ID NO: |
|---|---|---|---|---|---|
| | | $^{836}$ILSTLLCSL$^{841}$ | 13 | | |
| | | $^{926}$GLFPWCGLL$^{934}$ | 14 | | |
| | | $^{1072}$WLCHQAFLL$^{1080}$ | 15 | | |
| | | $^{572}$RLFFYRKSY$^{580}$ | 16 | | |

The peptide selection was confirmed using the application available online at the web site of the Bioinformatics & Molecular Analysis Section of NIH (bimas.dcrt.nih.gov/molbio/hla-bind/index.html) that ranks potential 9mer peptides based on a predicted half-time dissociation from HLA class I molecules deduced from (58). In our pilot studies one of the peptides identified using the "manual" approach—P865—ranked among the top HLA-A2-binding peptides identified through the software-guided analysis. Another peptide—P540—ranked at the top in the software-guided analysis.

Applicant used two such peptides 540ILAKFLHWL549 (SEQ ID NO:1) and 865RLVDDFLLV873 (SEQ ID NO:2), denoted as p540 and p865. Both peptides are able to induce a CTL response in vitro in normal blood donors and in patients with prostate cancer. Applicant has demonstrated that the same peptides are also able to induce a CTL response in vitro in patients with melanoma. A synopsis of these studies is shown in Table V.

Collectively, it appears that p540 induced a CTL response in 3 out of 4 HLA-A2+ patients. P865 induced a response in two patients only. It should be noted that patient 00 was concomitantly being immunized with dendritic cells+melanoma peptides (peptides other than hTRT peptides) and had a high background making it difficult to decided whether a specific response to hTRT had been induced.

TABLE V

INDUCTION OF CTL IN VITRO PATIENTS WITH MELANOMA

| Patient Code | CTL to p540 | CTL to p865 | Comments |
|---|---|---|---|
| 28-7 | 50% | 14% | |
| 00 | <5% | <5% | Concomitantly immunized with DC; High background |
| 66-5 | 49%* | 1% | *Measurable NK activity (17%) |
| 22-1 | 40% | 43% | |

Additional new findings came from exploring the immunogenicity of other hTRT peptides. In particular, three peptides were tested whose sequence in the native hTRT molecules is shown below in Table VI:

TABLE VI

ADDITIONAL SEQUENCE OF WILD TYPE AND MODIFIED HTRT PEPTIDES

| Name of Peptide | Wild Type Sequence | SEQ ID NO: | Modified Sequence | SEQ ID NO: |
|---|---|---|---|---|
| p152 | $^{152}$LLARCALFV$^{160}$ | 8 | $^{152}$YLARCALFV$^{160}$ | 18 |
| p555 | $^{555}$ELLRSFFYV$^{563}$ | 19 | $^{555}$YLLRSFFYV$^{563}$ | 20 |
| p572 | $^{572}$RLFFYRKSV$^{580}$ | 21 | $^{572}$YLFFYRKSV$^{580}$ | 22 |

Unlike p540, which was characterized as having a high affinity binding (slow half time dissociation) to HLA-A2 (Table VII), these peptides have an estimated half time dissociation score faster than prototype p540. Calculations we're made using the program (bimas.dcrt.nih.gov/molbio/hla_bind/index.html).

Applicant then proceeded to add a single residue (Y) modification in position 1, which is supposed to increase the binding affinity to HLA-A2 and also its immunogenicity (60). The new modified sequences are shown in Table VI.

PBMC from three normal HLA-A2+ individuals were immunized with the Y-modified peptides. The results are summarized as follows (Table VII).

Figure 6:
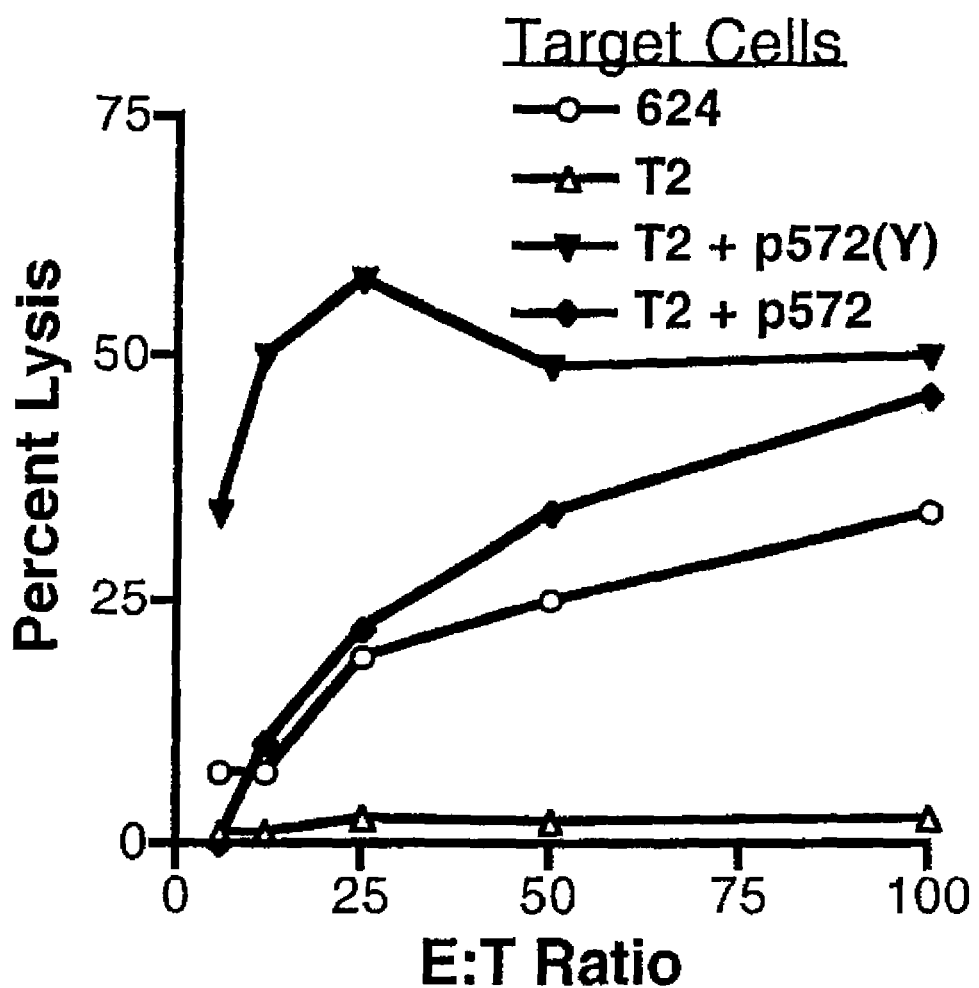
FIG. 6. Normal blood donor PBMC immunized in vitro against p572(Y) peptide of hTRT generate CTL that kill melanoma cells 624. The results are expressed as percent lysis and show by comparison lysis of 624 melanoma cells, and HLA-A2+T2 target cells pulsed with the p572(Y) and p572 wild type peptides, respectively. Nonspecific lysis of T2 cells is shown as a control.

CTL generated against p572 were also able to lyze the hTRT+/HLA-A2+ melanoma cell line 624. The dose response curve of killing of melanoma 624 is shown in FIG. 6. The antigen-recognition activity of T cells is intimately linked with recognition of MHC (HLA in humans) molecules.

Discussion

Applicant has demonstrated that hTRT peptides can expand precursor CTL in PBMC of normal individuals and patients with prostate cancer, and induce in both instances MHC Class I-restricted, peptide-specific CTL responses.

TABLE VII

THE IMMUNOGENIC CAPABILITY OF "Y" MODIFIED HTRT PEPTIDES.

| | | CTL Against Target Cells pulsed With . . . | | | |
|---|---|---|---|---|---|
| Donor | Immunogen | p152(Y) | p555(Y) | p572(Y) | p572 wild type |
| 218 | p152(Y) | 7% | | | |
| | p555(Y) | | 4% | | |
| | p572(Y) | | | 48-50% | 26-46% |
| 219 | p152(Y) | 2% | | | |
| | p555(Y) | | 8% | | |
| | p572(Y) | | | 4% | |
| 222 | p152(Y) | 1% | | | |
| | p555(Y) | | 1% | | |
| | p572(Y) | | | 27% | 5% |

Therefore, the first major implication from these findings is that the available CTL repertoire for hTRT is similarly preserved not only in normal individuals as recently reported (24) but also, and more importantly, in individuals with cancer. This suggests that exposure to cancer does not cause deletion or anergy of clonotypes specific for hTRT. Since the three patients responding to immunization were resistant to hormone therapy and had metastases, it was surprising that hTRT CTL could be induced at such an advanced stage of disease generally characterized by immunosuppression. Based on these considerations, one could predict that since the frequency of precursors from PBMC is high enough to permit their expansion in vitro and because hTRT peptides bind to MHC Class I with sufficient avidity, the two peptides identified in this study may be used for vaccination of HLA-A2+ cancer patients.

The finding that prostate cancer patients' CTL mediate efficient lysis of a variety of HLA-A2+ cancer cells such as prostate, breast, colon, lung and melanoma is unprecedented. Based on the values of specific lysis it appears as if these cancer cells are equally effective in processing and presenting the same endogenous hTRT peptides. Therefore, a second major implication of our study is that similar hTRT peptides are expressed and complexed with MHC Class I molecules on a variety of cancer cells of different histological origins and types. This renders them susceptible to destruction by CTL and underscores the potential advantage hTRT immunization may have in the control of primary tumors and metastases in a large variety of cancer types in humans.

The future of hTRT-based vaccination will also depend on the type of side effects that may follow immunization. Since hTRT is expressed in stem cells and mature hemopoietic cells (6, 7, 38), the possibility exists that hTRT vaccination could result in autoimmunity and destruction of normal cells. In our hands cancer patients' CTL specific for either p540 or p865 failed to lyse HLA-A2+ CD34+ cells. Similarly, CTL against p540 raised in normal individuals did not lyse HLA-A2+ CD34+ cells (24). Together with the lack of overt autoimmune defects in hemopoietic cells and in the liver in HHD mice following vaccination with hTRT peptides, Applicant provisionally concludes that CTL specific for hTRT are unlikely to trigger autoimmunity against normal cells. Possibly, the quantity of hTRT peptides generated under physiological lineage/clonotype activation and differentiation is insufficient to mediate lysis by CTL. Whether the same holds true for germ cells of reproductive organs for which little is known about CD8 T cell mediated autoimmunity, can only be speculated. While additional experiments are needed, the fact that autoimmunity does not develop after immunization against tumor antigens shared by normal tissues (48, 49), including the lymphoid tissue (50) and reproductive organs (51), supports the view that hTRT-based vaccination in cancer patients may be possible and safe.

Methods to implement such hTRT-based vaccination will include the variety of methods currently in use, such as synthetic peptides, synthetic peptides in immunological adjuvant, dendritic cells pulsed with synthetic peptides, naked DNA and RNA. In addition, Applicant anticipates that effective vaccination can be achieved using transgenic cells. For instance, genes under a specific lymphocyte promoter can be engineered to code for desired hTRT peptides, transfected and expressed in lymphocytes from an individual (e.g., a cancer patient), and the patient's own lymphocytes can be used for vaccination, since lymphocytes process and present peptides to T lymphocytes, hence effecting vaccination.

In conclusion, based on the demonstration that precursor CTL specific for two hTRT peptides can be expanded in patients with cancer, their CTL recognize the same hTRT peptides on tumor cells of various origins and histological types, and a strong in vivo CTL response against both hTRT peptides was induced in HLA-A2.1+ monochain transgenic mice, Applicant suggests that hTRT can be regarded as a universal cancer, antigen and its peptides as the substrate for a possible universal cancer vaccine for humans.

In accordance with the preceding explanation, variations and adaptations of the vaccine and methodology of the present invention will suggest themselves to a skilled practitioner in the medical arts, In the spirit of this invention, these and other possible variations and adaptations of the present invention, and the scope of the invention, should be determined in accordance with the following claims, only, and not solely in accordance with that embodiment within which the invention has been taught.

REFERENCES

1. Blackburn, E. H. (1992) Ann. Rev. Biochem 61, 113-29.
2. Blackburn, E. H. (1991) Nature 3 50, 569-73.
3. Greider, C. W. (1994) Curr. Opin. Oenet. Dvel. 4, 203-11.
4. Counter, C. M., Avilion, A. A., LeFeuvre, C. E., Stewart, N. G., Greider, C. W., Harley, C. B. & Bacchetti, S. (1992) EMBO J 11, 1921-9.
5. Buchkovich, K. J. & Greider, C. W. (1996) Mol. Biol. Cell 7, 1443-54.
6. Weng, N. P., Levine, B. L., June, C. H. & Hodes, R. J. (1996) J. Exp. Med. 183, 2471-9.
7. Weng, N. P., Granger, L. & Hodes, R. J. (1997) Proc. Natl. Acad. Sci. USA 94, 10827-32.
8. Lee, H. W., Blasco, M. A., Gottlieb, G. J., Horner, J. W., 2nd, Greider, C. W. & DePinho, R. A. (1998) Nature 392, 569-74.
9. Kim, N. W., Piatyszek, M. A., Prowse, K. R., Harley, C. B., West, M. D., Ho, P. L., Coviello, G. M., Wright, W. E., Weinrich, S. L. & Shay, J. W. (1994) Science 266, 2011-5.
10. Meyerson, M., Counter, C. M., Eaton, E. N., Ellisen, L. W., Steiner, P., Caddle, S. D., Ziaugra, L., Beijersbergen, R. L., Davidoff, M. J., Liu, Q., Bacchetti, S., Haber, D. A. & Weinberg, R. A. (1997) Cell 90, 785-95.
11. Bodnar, A. G., Ouellette, M., Frolkis, M., Holt, S. E., Chiu, C. P., Morin, G. B., Harley, C. B., Shay, J. W., Lichtsteiner, S. & Wright, W. E. (1998) Science 279, 349-52.
12. Rudolph, K. L., Chang, S., Lee, H. W., Blasco, M., Gottlieb, G. J., Greider, C. & DePinho, R. A. (1999) Cell 96, 701-12.
13. Greenberg, R. A., Chin, L., Femino, A., Lee, K. H., Gottlieb, G. J., Singer, R. H., Greider, C. W. & DePinho, R. A. (1999) Cell 97, 515-25.
14. Morales, C. P., Holt, S. E., Ouellette, M., Kaur, K. J., Yan, Y., Wilson, K. S., White, M. A., Wright, W. E. & Shay, J. W. (1999) Nature Genetics 21, 115-8.
15. Hahn, W. C., Counter, C. M., Lundberg, A. S., Beijersbergen, R. L., Brooks, M. W. & Weinberg, R. A. (1999) Nature 400, 464-8.
16. Broccoli, D., Young, J. W. & de Lange, T. (1995) Proc. Natl. Acad. Sci. USA 92, 9082-6.
17. Shay, J. W. & Bacchetti, S. (1997) Eur. J. Cancer 33, 787-91.
18. Kim, N. W. (1997) Eur. J. Cancer 33, 781-6.
19. Nakamura, T. M., Morin, G. B., Chapman, K. B., Weinrich, S. L., Andrews, W. H., Lingner, J., Harley, C. B. & Cech, T. R. (1997) Science 277, 955-9.
20. Marx, J. (1993) Science 262, 1644-5.
21. Disis, M. L. & Cheever, M. A. (1997) Adv. Cancer Res 71, 343-71.
22. Walker, B. D., Flexner, C., Paradis, T. J., Fuller, T. C., Hirsch, M. S., Schooley, R. T. & Moss, B. (1988) Science 240, 64-6.
23. Schwartz, R. H. (1990) Science 248, 1349-56.
24. Vonderheide, R. H., Hahn, W. C., Schultze, J. L. & Nadler, L. M. (1999) Immunity 10, 673-9.
25. Firat, H., Garcia-Pons, F., Tourdot, S., Pascolo, S., Scardino, A., Garcia, Z., Michel, M.-L., Jack, R., Jung, G., Kostmatopoulos, K., Mateo, L., Suhbrbier, A., Lemonnier, F. & Langlade-Demoyen, P. (1999) Eur. J. Immunol. 29, 3112-3121.
26. Lee, T. D. (1990) in The HLA System, ed. Lee, J. (Springer-Verlag, New York), pp. 141-178.
27. Fernandez-Vina, M. A., Falco, M., Sun, Y. & Stastny, P. (1992) Human Immunol. 33, 163-73.
28. Krausa, P., Brywka, M., 3rd, Savage, D., Hui, K. M., Bunce, M., Ngai, J. L., Teo, D. L., Ong, Y. W., Barouch, D., Allsop, C. E. & et al. (1995) Tissue Antigens 45, 223-31.
29. Ruppert, J., Sidney, J., Celis, E., Kubo, R. T., Grey, H. M. & Sette, A. (1993) Cell 74, 929-37.
30. Parker, K. C., Bednarek, M. A. & Coligan, J. E. (1994) J. Immunol. 152, 163-75.
31. Vitiello, A., Marchesini, D., Furze, J., Sherman, L. A. & Chesnut, R. W. (1991) J. Exp. Med. 173, 1007-15.
32. Sette, A., Vitiello, A., Reherman, B., Fowler, P., Nayersina, R., Kast, W. M., Melief, C. J., Oseroff, C., Yuan, L., Ruppert, J. & et al. (1994) J. Immunol. 153, 5586-92.
33. van der Burg, S. H., Visseren, M. J., Brandt, R. M., Kast, W. M. & Melief, C. J. (1996) J. Immunol. 156, 3308-14.
34. Sommerfeld, H. J., Meeker, A. K., Piatyszek, M. A., Bova, G. S., Shay, J. W. & 20 Coffey, D. S. (1996) Cancer Research 56, 218-22.
35. Hunt, D. F., Henderson, R. A., Shabanowitz, J., Sakaguchi, K., Michel, H., Sevilir, N., Cox, A. L., Appella, E. & Engelhard, V. H. (1992) Science 255, 1261-3.
36. Quaranta, V., Zanetti, M. & Reisfeld, R. A. (1982) J. Exp. Med. 156, 1551-6.
37. Zanetti, M., Filaci, G., Lee, R. H., del Guercio, P., Rossi, F., Bacchetta, R., Stevenson, F., Barnaba, V. & Billetta, R. (1993) EMBO J. 12, 4375-4384.
38. Hiyama, K., Ffirai, Y., Kyoizumi, S., Akiyama, M., Hiyama, E., Piatyszek, M. A., Shay, J. W., Ishioka, S. & Yamakido, M. (1995) J. Immunol. 155, 3711-5.
39. Pascolo, S., Bervas, N., Ure, J. M., Smith, A. G., Lemonnier, F. A. & Perarnau, B. (1997) J Exp Med 185, 2043-51.
40. Doyle, A., Martin, W. J., Funa, K., Gazdar, A., Carney, D., Martin, S. E., Linnoila, I., Cuttitta, F., Mulshine, J., Bunn, P. & et al. (1985) 1 Exp. Med. 161, 1135-51.
41. Momburg, F., Degener, T., Bacchus, E., Moldenhauer, G., Heammerling, G. J. & Meoller, P. (1986) Int. J. Cancer 37, 179-84.
42. Restifo, N. P., Esquivel, F., Kawakami, Y., Yewdell, J. W., Mule, J. J., Rosenberg, S. A. & Bennink, J. R. (1993) J. Exp. Med. 177, 265-272.
43. Cromme, F. V., Airey, J., Heemels, M. T., Ploegh, H. L., Keating, P. J., Stem, P. L., Meijer, C. J. & Walboomers, J. M. (1994) J. Exp. Med. 179, 335-340.
44. Rosenberg, S. A., Yang, J. C., Schwartzentruber, D. J., Hwu, P., Marincola, F. M., Topalian, S. L., Restifo, N. P., Dudley, M. E., Schwarz, S. L., Spiess, P. J., Wunderlich, J. R., Parkhurst, M. R., Kawakami, Y., Seipp, C. A., Einhorn, J. H. & White, D. E. (1998) Nature Medicine 4, 321-327.
45. Nestle, F. O., Alijagic, S., Gilliet, M., Sun, M., Grabbe, S., Dummer, R., Burg, G. & Schadendorf, D. (1998) Nature Medicine 4, 328-332.
46. Thomson, S. A., Sherritt, M. A., Medveczky, J., Elliott, S. L., Moss, D. J., Fernando, G. J., Brown, L. E. & Suhrbier, A. (1998) J. Immunol. 160, 1717-23.
47. Sykulev, Y., Joo, M., Vturina, I., Tsomides, T. J. & Eisen, H. N. (1996) Immunity 4, 565-71.
48. Morgan, D. J., Krcuwd, H. T., Fleck, S., Levitsky, H. I., Pardoll, D. M. & Sherman, L. A. (1998) J. Immunol. 160, 643-51.
49. Overwijk, W. W., Lee, D. S., Surman, D. R., Irvine, K. R., Touloukian, C. E., Chan, C. C., Carroll, M. W., Moss, B., Rosenberg, S. A. & Restifo, N. P. (1999) Proc. Natl. Acad. Sci. USA 96, 2982-7.
50. Hu, J., Kindsvogel, W., Busby, S., Bailey, M. C., Shi, Y. Y. & Greenberg, P. D. (1993) J. Exp. Med. 177, 1681-90,
51. Uyttenhove, C., Godfraind, C., Lethae, B., Amar-Costesec, A., Renauld, J. C., Gajewski, T. F., Duffour, M. T., Warnier, G., Boon, T. & Van den Eynde, B. J. (1997) Int. J. Cancer 70, 349-56.
52. Falk, K., Rotzschke, O., Stevanovic, S., Jung, G., and Rammensee, H. G. (1991) Nature 351, 290-6.
53. Fernandez-Vina, M. A., Falco, M., Sun, Y., and Stastny, P. (1992), Human Immunology 33, 163-73.
54. Firat, H., Garcia-Pons, F., tourdot, S., Pascolo, S., Scardino, A., Garcia, Z., Michel, M.-L., Jack, R., Jung, G., Kostmatopoulos, K., Mateo, L., Suhrbrier, A., Lemonnier, F., and Langlade-Demoyen, P. (1999) Eur. J. Immunol. 29, 3112-3121.
55. Krausa, P., Brywka, M., 3rd, Savage, D., Hui, K. M., Bunce, M., Ngai, J. L., Teo, D. L., Ong, Y. W., Barouch, D., Allsop, C. E., and et al. (1995). Genetic polymorphism within HLA-A*02: significant allelic variation revealed in different populations. Tissue Antigens 45, 223-31.
56. Lee, T. D. (1990) In The HLA System, J. Lee, ed. (New York: Springer-Verlag), pp. 141-178.
57. Nakamura, T. M., Morin, G. B., Chapman, K. B., Weinrich, S. L., Andrews, W. H., Lingner, J., Harley, C. B., and Cech, T. R. (1997) [see comments]. Science 277, 955-9.
58. Parker, K. C., Bednarek, M. A., and Coligan, J. E. (1994) Journal of Immunology 152, 163-75.
59. Rotzschke, O., Falk, K., Deres, K., Schild, H., Norda, M., Metzger, J., Jung, G., and Rammensee, H.-G. (1990) Nature 348, 252-254.
60. Ruppert, J., Sidney, J., Celis, E., Kubo, R. T., Grey, H. M., and Sette, A. (1993) Cell 74, 929-37.
61. Schumacher, T. N., De Bruijn, M. L., Vernie, L. N., Kast, W. M., Melief, C. J., Neefjes, J. J., and Ploegh, H. L. (1991) Nature 350, 703-6.

The invention claimed is:

1. An isolated peptide consisting of the amino acid sequence of one and of the group consisting of SEQ ID NO:18 (pY152) and SEQ ID NO:20 (pY555), wherein the peptide induces or enhances a human telomerase reverse-transcriptase-reactive cytotoxic T lymphocyte response.

2. The isolated peptide of claim 1, consisting of the amino acid sequence of SEQ ID NO:18 (pY152).

3. The isolated peptide of claim 1, consisting of the amino acid sequence of SEQ ID NO:20 (pY555).

4. A composition comprising the isolated peptide of claim 1, and an isolated physiologically acceptable carrier.

5. The composition of claim 4, wherein said carrier is a mammalian cell.

6. A nucleic acid encoding a peptide consisting of the amino acid sequence selected from the group consisting of SEQ ID NO:18 (pY152), SEQ ID NO:20 (pY555), and SEQ ID NO:22 (pY572), wherein the peptide induces or enhances a human telomerase reverse-transcriptase-reactive cytotoxic T lymphocyte response.

7. The nucleic acid of claim 6, wherein said nucleic acid is DNA.

8. The nucleic acid of claim 6, wherein said nucleic acid is RNA.

9. An isolated host cell comprising the nucleic acid of claim 6.

10. The nucleic acid of claim 6, wherein said nucleic acid encodes a peptide consisting of the amino acid sequence of SEQ ID NO:18 (pY152).

11. The nucleic acid of claim 6, wherein said nucleic acid encodes a peptide consisting of the amino acid sequence of SEQ ID NO:20 (pY555).

12. The nucleic acid of claim 6, wherein said nucleic acid encodes a peptide consisting of the amino acid sequence of SEQ ID NO:22 (pY572).

* * * * *